United States Patent [19]

Baum et al.

[11] Patent Number: 5,457,035
[45] Date of Patent: Oct. 10, 1995

[54] CYTOKINE WHICH IS A LIGAND FOR OX40

[75] Inventors: Peter R. Baum, Seattle; William C. Fanslow, III, Federal Way; Richard B. Gayle, Woodinville; Raymond G. Goodwin, Seattle, all of Wash.

[73] Assignee: Immunex Corporation, Seattle, Wash.

[21] Appl. No.: 97,827

[22] Filed: Jul. 23, 1993

[51] Int. Cl.⁶ .......................... C12N 15/19; C07H 21/04
[52] U.S. Cl. .................. 435/69.5; 435/240.1; 435/252.3; 435/320.1; 536/23.5; 530/351; 935/9
[58] Field of Search .................. 435/69.1, 69.5, 435/240.1, 252.3, 320.1; 536/23.5

OTHER PUBLICATIONS

Cosmon, *Cytopine* vol. 5(2) 1993, pp. 95–106.
Kaczmarski et al., *Blood Review* 5, 1991, pp. 193–203.
Calderhead et al., J. Immunol. 151:5261–5271; 1993.
Paterson et al., *Mol. Immunol.* 24:1281; 1987.
Mallett et al., *EMBO J.* 9:1063, 1990.
Mallett and Barclay, *Immunology Today* 12:220; 1991.
Smith et al., *Biochem. Biophys. Res. Commun.* 176:335; 1991.
Miura et al., *Mol. Cell. Biol.* 11:1313; 1991.

*Primary Examiner*—Garnette D. Draper
*Assistant Examiner*—Lorraine M. Spector
*Attorney, Agent, or Firm*—Patricia Anne Perkins

[57] ABSTRACT

There is disclosed a polypeptide (OX40-L) and DNA sequences, vectors and transformed host cells useful in providing OX40-L polypeptides. More particularly, this invention provides isolated murine OX40-L polypeptides that bind to the extracellular binding region of OX40.

8 Claims, 4 Drawing Sheets

5,457,035

SEQUENCE LISTING ( 1 ) GENERAL INFORMATION:

5,457,035

-continued ( i i i ) NUMBER OF SEQUENCES: 13

( 2 ) INFORMATION FOR SEQ ID NO:1:

( i ) SEQUENCE CHARACTERISTICS:
    ( A ) LENGTH: 1633 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
    ( B ) CLONE: MUSOX40-L ( i x ) FEATURE:
    ( A ) NAME/KEY: CDS
    ( B ) LOCATION: 148..744

( x i ) SEQUENCE DESCRIPTION: SEQ ID NO:1:

```
AGATCTTGGA ACGAGACGAC CTGCTGGGAC CTTTATCTTC TGACCCGCAG GCTTGACTTT      60

GCCCTTATTG GCTCCTTTGT GGTGAAGAGC AGTCTTCCCC CAGGTTCCCC GCCACAGCTG     120

TATCTCCTCT GCACCCCGAC TGCAGAG ATG GAA GGG GAA GGG GTT CAA CCC        171
                              Met Glu Gly Glu Gly Val Gln Pro
                                1               5

CTG GAT GAG AAT CTG GAA AAC GGA TCA AGG CCA AGA TTC AAG TGG AAG      219
Leu Asp Glu Asn Leu Glu Asn Gly Ser Arg Pro Arg Phe Lys Trp Lys
         10              15                  20

AAG ACG CTA AGG CTG GTG GTC TCT GGG ATC AAG GGA GCA GGG ATG CTT      267
Lys Thr Leu Arg Leu Val Val Ser Gly Ile Lys Gly Ala Gly Met Leu
 25              30                  35                      40

CTG TGC TTC ATC TAT GTC TGC CTG CAA CTC TCT TCC TCT CCG GCA AAG      315
Leu Cys Phe Ile Tyr Val Cys Leu Gln Leu Ser Ser Ser Pro Ala Lys
                     45                  50                  55

GAC CCT CCA ATC CAA AGA CTC AGA GGA GCA GTT ACC AGA TGT GAG GAT      363
Asp Pro Pro Ile Gln Arg Leu Arg Gly Ala Val Thr Arg Cys Glu Asp
                 60                  65                  70

GGG CAA CTA TTC ATC AGC TCA TAC AAG AAT GAG TAT CAA ACT ATG GAG      411
Gly Gln Leu Phe Ile Ser Ser Tyr Lys Asn Glu Tyr Gln Thr Met Glu
             75                  80                  85

GTG CAG AAC AAT TCG GTT GTC ATC AAG TGT GAT GGG CTT TAT ATC ATC      459
Val Gln Asn Asn Ser Val Val Ile Lys Cys Asp Gly Leu Tyr Ile Ile
         90                  95                  100

TAC CTG AAG GGC TCC TTT TTC CAG GAG GTC AAG ATT GAC CTT CAT TTC      507
Tyr Leu Lys Gly Ser Phe Phe Gln Glu Val Lys Ile Asp Leu His Phe
105                  110                  115                 120

CGG GAG GAT CAT AAT CCC ATC TCT ATT CCA ATG CTG AAC GAT GGT CGA      555
Arg Glu Asp His Asn Pro Ile Ser Ile Pro Met Leu Asn Asp Gly Arg
                 125                  130                 135

AGG ATT GTC TTC ACT GTG GTG GCC TCT TTG GCT TTC AAA GAT AAA GTT      603
Arg Ile Val Phe Thr Val Val Ala Ser Leu Ala Phe Lys Asp Lys Val
             140                  145                 150

TAC CTG ACT GTA AAT GCT CCT GAT ACT CTC TGC GAA CAC CTC CAG ATA      651
Tyr Leu Thr Val Asn Ala Pro Asp Thr Leu Cys Glu His Leu Gln Ile
         155                 160                  165

AAT GAT GGG GAG CTG ATT GTT GTC CAG CTA ACG CCT GGA TAC TGT GCT      699
Asn Asp Gly Glu Leu Ile Val Val Gln Leu Thr Pro Gly Tyr Cys Ala
170                  175                  180
```

| CCT | GAA | GGA | TCT | TAC | CAC | AGC | ACT | GTG | AAC | CAA | GTA | CCA | CTG | TGAATTCCAC | 751 |
| Pro | Glu | Gly | Ser | Tyr | His | Ser | Thr | Val | Asn | Gln | Val | Pro | Leu | | |
| 185 | | | | 190 | | | | | 195 | | | | | | |

```
TCTGAGGGTG  GACGGGACAC  AGGTTCTTTC  TCGAGAGAGA  TGAGTGCATC  CTGCTCATGA    811
GATGTGACTG  AATGCAGAGC  CTACCCTACT  TCCTCACTCA  GGGATATTTA  AATCATGTCT    871
TACATAACAG  TTGACCTCTC  ATTCCCAGGA  TTGCCTTGAG  CCTGCTAAGA  GCTGTTCTGG    931
GAATGAAAAA  AAAATAAATG  TCTCTTCAAG  ACACATTGCT  TCTGTCGGTC  AGAAGCTCAT    991
CGTAATAAAC  ATCTGCCACT  GAAAATGGCG  CTTGATTGCT  ATCTTCTAGA  ATTTTGATGT   1051
TGTCAAAAGA  AAGCAAAACA  TGGAAAGGGT  GGTGTCCACC  AGCCAGTAGG  AGCTGGAGTG   1111
CTCTCTCCAG  GTTAAGGTGA  TAGAAGTTTA  CATGTTGCCT  AAAACTGTCT  CTCATCTCAT   1171
GGGGGGCTTG  GAAAGAAGAT  TACCCCGTGG  AAAGCAGGAC  TTGAAGATGA  CTGTTTAAGC   1231
AACAAGGTGC  ACTCTTTTCC  TGGCCCCTGA  ATACACATAA  AAGACAACTT  CCTTCAAAGA   1291
ACTACCTAGG  GACTATGATA  CCCACCAAAG  AACCACGTCA  GCGATGCAAA  GAAAACCAGG   1351
AGAGCTTTGT  TTATTTTGCA  GAGTATACGA  GAGATTTTTA  CCCTGAGGGC  TATTTTTATT   1411
ATACAGAATG  ATAGTGAACT  GGATGTCTCA  GGATAAAGGC  CAAGAAGGAT  TTTTCACAGT   1471
CTGAGCAAGA  CTGTTTTTGT  AGGTTTCTCT  CTCCAAAACT  TTTAGGTAAA  TTTTTGATAA   1531
TTTTTAAATT  TTTATATTTT  TGGACCATTT  TCAATAGAAG  ATTGAAACAT  TTCCAGATGG   1591
TTTCATATCC  CCACAAGAGC  AGGTCGTCTC  GTTCCAAGAT  CT                       1633
```

( 2 ) INFORMATION FOR SEQ ID NO:2:

( i ) SEQUENCE CHARACTERISTICS:
        ( A ) LENGTH: 198 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Gly  Glu  Gly  Val  Gln  Pro  Leu  Asp  Glu  Asn  Leu  Glu  Asn  Gly
 1              5                        10                       15

Ser  Arg  Pro  Arg  Phe  Lys  Trp  Lys  Lys  Thr  Leu  Arg  Leu  Val  Val  Ser
               20                       25                       30

Gly  Ile  Lys  Gly  Ala  Gly  Met  Leu  Leu  Cys  Phe  Ile  Tyr  Val  Cys  Leu
               35                       40                       45

Gln  Leu  Ser  Ser  Ser  Pro  Ala  Lys  Asp  Pro  Pro  Ile  Gln  Arg  Leu  Arg
     50                       55                       60

Gly  Ala  Val  Thr  Arg  Cys  Glu  Asp  Gly  Gln  Leu  Phe  Ile  Ser  Ser  Tyr
65                       70                       75                       80

Lys  Asn  Glu  Tyr  Gln  Thr  Met  Glu  Val  Gln  Asn  Asn  Ser  Val  Val  Ile
                    85                       90                       95

Lys  Cys  Asp  Gly  Leu  Tyr  Ile  Ile  Tyr  Leu  Lys  Gly  Ser  Phe  Phe  Gln
                    100                      105                      110

Glu  Val  Lys  Ile  Asp  Leu  His  Phe  Arg  Glu  Asp  His  Asn  Pro  Ile  Ser
          115                      120                      125

Ile  Pro  Met  Leu  Asn  Asp  Gly  Arg  Arg  Ile  Val  Phe  Thr  Val  Val  Ala
     130                      135                      140

Ser  Leu  Ala  Phe  Lys  Asp  Lys  Val  Tyr  Leu  Thr  Val  Asn  Ala  Pro  Asp
145                      150                      155                      160

Thr  Leu  Cys  Glu  His  Leu  Gln  Ile  Asn  Asp  Gly  Glu  Leu  Ile  Val  Val
                    165                      170                      175
```

Gln Leu Thr Pro Gly Tyr Cys Ala Pro Glu Gly Ser Tyr His Ser Thr
            180                 185                 190

Val Asn Gln Val Pro Leu
            195

( 2 ) INFORMATION FOR SEQ ID NO:3:

( i ) SEQUENCE CHARACTERISTICS:
       ( A ) LENGTH: 31 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
       ( B ) CLONE: Oligo 6142

( x i ) SEQUENCE DESCRIPTION: SEQ ID NO:3:

GTCACTAGTC ACCATGTATG TGTGGGTTCA G                                    31

( 2 ) INFORMATION FOR SEQ ID NO:4:

( i ) SEQUENCE CHARACTERISTICS:
       ( A ) LENGTH: 26 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
       ( B ) CLONE: Oligo 6163

( x i ) SEQUENCE DESCRIPTION: SEQ ID NO:4:

CAGACTAGTT CAGATCTTGG CTAGAG                                          26

( 2 ) INFORMATION FOR SEQ ID NO:5:

( i ) SEQUENCE CHARACTERISTICS:
       ( A ) LENGTH: 33 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
       ( B ) CLONE: Oligo 6162

( x i ) SEQUENCE DESCRIPTION: SEQ ID NO:5:

CACAAGATCT GGGCTCCACC AAGGTGGGTG TAG                                  33

( 2 ) INFORMATION FOR SEQ ID NO:6:

( i ) SEQUENCE CHARACTERISTICS:
       ( A ) LENGTH: 618 base pairs
       ( B ) TYPE: nucleic acid
       ( C ) STRANDEDNESS: single (D) TOPOLOGY: linear (ii) MOLECULE TYPE: cDNA to mRNA (iii) HYPOTHETICAL: NO (iv) ANTI-SENSE: NO (vii) IMMEDIATE SOURCE:
    (B) CLONE: MOUSE OX40

(ix) FEATURE:
    (A) NAME/KEY: CDS
    (B) LOCATION: 1..618

(xi) SEQUENCE DESCRIPTION: SEQ ID NO:6:

| ATG | TAT | GTG | TGG | GTT | CAG | CAG | CCC | ACA | GCC | CTT | CTG | CTG | CTG | GGA | CTC | 48 |
| Met | Tyr | Val | Trp | Val | Gln | Gln | Pro | Thr | Ala | Leu | Leu | Leu | Leu | Gly | Leu | |
| 1 | | | | 5 | | | | | 10 | | | | | 15 | | |

| ACA | CTT | GGA | GTT | ACA | GCA | AGG | CGG | CTC | AAC | TGT | GTT | AAA | CAT | ACC | TAC | 96 |
| Thr | Leu | Gly | Val | Thr | Ala | Arg | Arg | Leu | Asn | Cys | Val | Lys | His | Thr | Tyr | |
| | | | 20 | | | | | 25 | | | | | 30 | | | |

| CCC | AGT | GGT | CAC | AAG | TGC | TGT | CGT | GAG | TGC | CAG | CCA | GGC | CAT | GGT | ATG | 144 |
| Pro | Ser | Gly | His | Lys | Cys | Cys | Arg | Glu | Cys | Gln | Pro | Gly | His | Gly | Met | |
| | | 35 | | | | 40 | | | | | 45 | | | | | |

| GTG | AAC | CGC | TGT | GAT | CAT | ACC | AGG | GAT | ACT | CTA | TGT | CAT | CCG | TGT | GAG | 192 |
| Val | Asn | Arg | Cys | Asp | His | Thr | Arg | Asp | Thr | Leu | Cys | His | Pro | Cys | Glu | |
| | 50 | | | | | 55 | | | | | 60 | | | | | |

| ACT | GGC | TTC | TAC | AAT | GAA | GCT | GTC | AAT | TAT | GAT | ACC | TGC | AAG | CAG | TGT | 240 |
| Thr | Gly | Phe | Tyr | Asn | Glu | Ala | Val | Asn | Tyr | Asp | Thr | Cys | Lys | Gln | Cys | |
| 65 | | | | | 70 | | | | | 75 | | | | | 80 | |

| ACA | CAG | TGC | AAC | CAT | CGA | AGT | GGA | AGT | GAA | CTC | AAG | CAG | AAT | TGC | ACA | 288 |
| Thr | Gln | Cys | Asn | His | Arg | Ser | Gly | Ser | Glu | Leu | Lys | Gln | Asn | Cys | Thr | |
| | | | | 85 | | | | | 90 | | | | | 95 | | |

| CCT | ACT | CAG | GAT | ACT | GTC | TGC | AGA | TGT | AGA | CCA | GGC | ACC | CAA | CCT | CGG | 336 |
| Pro | Thr | Gln | Asp | Thr | Val | Cys | Arg | Cys | Arg | Pro | Gly | Thr | Gln | Pro | Arg | |
| | | | 100 | | | | | 105 | | | | | 110 | | | |

| CAG | GAC | AGC | GGC | TAC | AAG | CTT | GGA | GTT | GAC | TGT | GTT | CCC | TGC | CCT | CCT | 384 |
| Gln | Asp | Ser | Gly | Tyr | Lys | Leu | Gly | Val | Asp | Cys | Val | Pro | Cys | Pro | Pro | |
| | | 115 | | | | | 120 | | | | | 125 | | | | |

| GGC | CAC | TTT | TCT | CCA | GGC | AAC | AAC | CAG | GCC | TGC | AAG | CCC | TGG | ACC | AAT | 432 |
| Gly | His | Phe | Ser | Pro | Gly | Asn | Asn | Gln | Ala | Cys | Lys | Pro | Trp | Thr | Asn | |
| | 130 | | | | | 135 | | | | | 140 | | | | | |

| TGT | ACC | TTA | TCT | GGA | AAG | CAG | ACC | CGC | CAC | CCA | GCC | AGT | GAC | AGC | TTG | 480 |
| Cys | Thr | Leu | Ser | Gly | Lys | Gln | Thr | Arg | His | Pro | Ala | Ser | Asp | Ser | Leu | |
| 145 | | | | | 150 | | | | | 155 | | | | | 160 | |

| GAC | GCA | GTC | TGT | GAG | GAC | AGA | AGC | CTC | CTG | GCC | ACA | CTG | CTC | TGG | GAG | 528 |
| Asp | Ala | Val | Cys | Glu | Asp | Arg | Ser | Leu | Leu | Ala | Thr | Leu | Leu | Trp | Glu | |
| | | | | 165 | | | | | 170 | | | | | 175 | | |

| ACC | CAG | CGC | CCT | ACA | TTC | AGG | CCA | ACC | ACT | GTC | CAA | TCC | ACC | ACA | GTC | 576 |
| Thr | Gln | Arg | Pro | Thr | Phe | Arg | Pro | Thr | Thr | Val | Gln | Ser | Thr | Thr | Val | |
| | | | 180 | | | | | 185 | | | | | 190 | | | |

| TGG | CCC | AGG | ACT | TCT | GAG | TTG | CCC | TCT | ACA | CCC | ACC | TTG | GTG | | | 618 |
| Trp | Pro | Arg | Thr | Ser | Glu | Leu | Pro | Ser | Thr | Pro | Thr | Leu | Val | | | |
| | | 195 | | | | | 200 | | | | | 205 | | | | |

(2) INFORMATION FOR SEQ ID NO:7:

(i) SEQUENCE CHARACTERISTICS:
    (A) LENGTH: 206 amino acids
    (B) TYPE: amino acid
    (D) TOPOLOGY: linear (ii) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met<br>1 | Tyr | Val | Trp | Val<br>5 | Gln | Gln | Pro | Thr | Ala<br>10 | Leu | Leu | Leu | Leu | Gly<br>15 | Leu |
| Thr | Leu | Gly | Val<br>20 | Thr | Ala | Arg | Arg | Leu | Asn<br>25 | Cys | Val | Lys | His<br>30 | Thr | Tyr |
| Pro | Ser | Gly<br>35 | His | Lys | Cys | Cys | Arg<br>40 | Glu | Cys | Gln | Pro | Gly<br>45 | His | Gly | Met |
| Val | Asn<br>50 | Arg | Cys | Asp | His | Thr<br>55 | Arg | Asp | Thr | Leu | Cys<br>60 | His | Pro | Cys | Glu |
| Thr<br>65 | Gly | Phe | Tyr | Asn | Glu<br>70 | Ala | Val | Asn | Tyr | Asp<br>75 | Thr | Cys | Lys | Gln | Cys<br>80 |
| Thr | Gln | Cys | Asn | His<br>85 | Arg | Ser | Gly | Ser | Glu<br>90 | Leu | Lys | Gln | Asn | Cys<br>95 | Thr |
| Pro | Thr | Gln | Asp<br>100 | Thr | Val | Cys | Arg | Cys<br>105 | Arg | Pro | Gly | Thr | Gln<br>110 | Pro | Arg |
| Gln | Asp | Ser<br>115 | Gly | Tyr | Lys | Leu | Gly<br>120 | Val | Asp | Cys | Val | Pro<br>125 | Cys | Pro | Pro |
| Gly | His<br>130 | Phe | Ser | Pro | Gly | Asn<br>135 | Asn | Gln | Ala | Cys | Lys<br>140 | Pro | Trp | Thr | Asn |
| Cys<br>145 | Thr | Leu | Ser | Gly | Lys<br>150 | Gln | Thr | Arg | His | Pro<br>155 | Ala | Ser | Asp | Ser | Leu<br>160 |
| Asp | Ala | Val | Cys | Glu<br>165 | Asp | Arg | Ser | Leu | Leu<br>170 | Ala | Thr | Leu | Leu | Trp<br>175 | Glu |
| Thr | Gln | Arg | Pro<br>180 | Thr | Phe | Arg | Pro | Thr<br>185 | Thr | Val | Gln | Ser | Thr<br>190 | Thr | Val |
| Trp | Pro | Arg<br>195 | Thr | Ser | Glu | Leu | Pro<br>200 | Ser | Thr | Pro | Thr | Leu<br>205 | Val | | |

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Oligo NOPVU1

( x i ) SEQUENCE DESCRIPTION: SEQ ID NO:8:

CTTCTGACAA CTATAGGCGG ACCGAAGG        28

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:

5,457,035

-continued (B) CLONE: Oligo NOFCR1

(xi) SEQUENCE DESCRIPTION: SEQ ID NO:9:

CCAGCACCT GAAGCCGAGG GCGCGCCGTC AGTCTTCC                          38

(2) INFORMATION FOR SEQ ID NO:10:

(i) SEQUENCE CHARACTERISTICS:
      (A) LENGTH: 1317 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: MOX40Fc Mutein (ix) FEATURE:
      (A) NAME/KEY: CDS
      (B) LOCATION: 1..1317

(xi) SEQUENCE DESCRIPTION: SEQ ID NO:10:

```
ATG  TAT  GTG  TGG  GTT  CAG  CAG  CCC  ACA  GCC  CTT  CTG  CTG  CTG  GGA  CTC      48
Met  Tyr  Val  Trp  Val  Gln  Gln  Pro  Thr  Ala  Leu  Leu  Leu  Leu  Gly  Leu
 1                    5                        10                       15

ACA  CTT  GGA  GTT  ACA  GCA  AGG  CGG  CTC  AAC  TGT  GTT  AAA  CAT  ACC  TAC      96
Thr  Leu  Gly  Val  Thr  Ala  Arg  Arg  Leu  Asn  Cys  Val  Lys  His  Thr  Tyr
                 20                      25                      30

CCC  AGT  GGT  CAC  AAG  TGC  TGT  CGT  GAG  TGC  CAG  CCA  GGC  CAT  GGT  ATG     144
Pro  Ser  Gly  His  Lys  Cys  Cys  Arg  Glu  Cys  Gln  Pro  Gly  His  Gly  Met
             35                      40                      45

GTG  AAC  CGC  TGT  GAT  CAT  ACC  AGG  GAT  ACT  CTA  TGT  CAT  CCG  TGT  GAG     192
Val  Asn  Arg  Cys  Asp  His  Thr  Arg  Asp  Thr  Leu  Cys  His  Pro  Cys  Glu
         50                      55                      60

ACT  GGC  TTC  TAC  AAT  GAA  GCT  GTC  AAT  TAT  GAT  ACC  TGC  AAG  CAG  TGT     240
Thr  Gly  Phe  Tyr  Asn  Glu  Ala  Val  Asn  Tyr  Asp  Thr  Cys  Lys  Gln  Cys
65                       70                      75                      80

ACA  CAG  TGC  AAC  CAT  CGA  AGT  GGA  AGT  GAA  CTC  AAG  CAG  AAT  TGC  ACA     288
Thr  Gln  Cys  Asn  His  Arg  Ser  Gly  Ser  Glu  Leu  Lys  Gln  Asn  Cys  Thr
                 85                      90                      95

CCT  ACT  CAG  GAT  ACT  GTC  TGC  AGA  TGT  AGA  CCA  GGC  ACC  CAA  CCT  CGG     336
Pro  Thr  Gln  Asp  Thr  Val  Cys  Arg  Cys  Arg  Pro  Gly  Thr  Gln  Pro  Arg
            100                     105                     110

CAG  GAC  AGC  GGC  TAC  AAG  CTT  GGA  GTT  GAC  TGT  GTT  CCC  TGC  CCT  CCT     384
Gln  Asp  Ser  Gly  Tyr  Lys  Leu  Gly  Val  Asp  Cys  Val  Pro  Cys  Pro  Pro
            115                     120                     125

GGC  CAC  TTT  TCT  CCA  GGC  AAC  AAC  CAG  GCC  TGC  AAG  CCC  TGG  ACC  AAT     432
Gly  His  Phe  Ser  Pro  Gly  Asn  Asn  Gln  Ala  Cys  Lys  Pro  Trp  Thr  Asn
         130                     135                     140

TGT  ACC  TTA  TCT  GGA  AAG  CAG  ACC  CGC  CAC  CCA  GCC  AGT  GAC  AGC  TTG     480
Cys  Thr  Leu  Ser  Gly  Lys  Gln  Thr  Arg  His  Pro  Ala  Ser  Asp  Ser  Leu
145                      150                     155                     160

GAC  GCA  GTC  TGT  GAG  GAC  AGA  AGC  CTC  CTG  GCC  ACA  CTG  CTC  TGG  GAG     528
Asp  Ala  Val  Cys  Glu  Asp  Arg  Ser  Leu  Leu  Ala  Thr  Leu  Leu  Trp  Glu
                 165                     170                     175

ACC  CAG  CGC  CCT  ACA  TTC  AGG  CCA  ACC  ACT  GTC  CAA  TCC  ACC  ACA  GTC     576
Thr  Gln  Arg  Pro  Thr  Phe  Arg  Pro  Thr  Thr  Val  Gln  Ser  Thr  Thr  Val
            180                     185                     190

TGG  CCC  AGG  ACT  TCT  GAG  TTG  CCC  TCT  ACA  CCC  ACC  TTG  GTG  GAG  CCC     624
```

```
Trp  Pro  Arg  Thr  Ser  Glu  Leu  Pro  Ser  Thr  Pro  Thr  Leu  Val  Glu  Pro
     195                      200                 205

AGA  TCT  TGT  GAC  AAA  ACT  CAC  ACA  TGC  CCA  CCG  TGC  CCA  GCA  CCT  GAA     672
Arg  Ser  Cys  Asp  Lys  Thr  His  Thr  Cys  Pro  Pro  Cys  Pro  Ala  Pro  Glu
     210                      215                 220

GCC  GAG  GGC  GCG  CCG  TCA  GTC  TTC  CTC  TTC  CCC  CCA  AAA  CCC  AAG  GAC     720
Ala  Glu  Gly  Ala  Pro  Ser  Val  Phe  Leu  Phe  Pro  Pro  Lys  Pro  Lys  Asp
225                           230                 235                      240

ACC  CTC  ATG  ATC  TCC  CGG  ACC  CCT  GAG  GTC  ACA  TGC  GTG  GTG  GTG  GAC     768
Thr  Leu  Met  Ile  Ser  Arg  Thr  Pro  Glu  Val  Thr  Cys  Val  Val  Val  Asp
                    245                      250                      255

GTG  AGC  CAC  GAA  GAC  CCT  GAG  GTC  AAG  TTC  AAC  TGG  TAC  GTG  GAC  GGC     816
Val  Ser  His  Glu  Asp  Pro  Glu  Val  Lys  Phe  Asn  Trp  Tyr  Val  Asp  Gly
               260                      265                      270

GTG  GAG  GTG  CAT  AAT  GCC  AAG  ACA  AAG  CCG  CGG  GAG  GAG  CAG  TAC  AAC     864
Val  Glu  Val  His  Asn  Ala  Lys  Thr  Lys  Pro  Arg  Glu  Glu  Gln  Tyr  Asn
          275                      280                      285

AGC  ACG  TAC  CGG  GTG  GTC  AGC  GTC  CTC  ACC  GTC  CTG  CAC  CAG  GAC  TGG     912
Ser  Thr  Tyr  Arg  Val  Val  Ser  Val  Leu  Thr  Val  Leu  His  Gln  Asp  Trp
     290                      295                      300

CTG  AAT  GGC  AAG  GAG  TAC  AAG  TGC  AAG  GTC  TCC  AAC  AAA  GCC  CTC  CCA     960
Leu  Asn  Gly  Lys  Glu  Tyr  Lys  Cys  Lys  Val  Ser  Asn  Lys  Ala  Leu  Pro
305                           310                 315                      320

GCC  CCC  ATC  GAG  AAA  ACC  ATC  TCC  AAA  GCC  AAA  GGG  CAG  CCC  CGA  GAA    1008
Ala  Pro  Ile  Glu  Lys  Thr  Ile  Ser  Lys  Ala  Lys  Gly  Gln  Pro  Arg  Glu
                    325                      330                      335

CCA  CAG  GTG  TAC  ACC  CTG  CCC  CCA  TCC  CGG  GAT  GAG  CTG  ACC  AAG  AAC    1056
Pro  Gln  Val  Tyr  Thr  Leu  Pro  Pro  Ser  Arg  Asp  Glu  Leu  Thr  Lys  Asn
               340                      345                      350

CAG  GTC  AGC  CTG  ACC  TGC  CTG  GTC  AAA  GGC  TTC  TAT  CCC  AGC  GAC  ATC    1104
Gln  Val  Ser  Leu  Thr  Cys  Leu  Val  Lys  Gly  Phe  Tyr  Pro  Ser  Asp  Ile
          355                      360                      365

GCC  GTG  GAG  TGG  GAG  AGC  AAT  GGG  CAG  CCG  GAG  AAC  AAC  TAC  AAG  ACC    1152
Ala  Val  Glu  Trp  Glu  Ser  Asn  Gly  Gln  Pro  Glu  Asn  Asn  Tyr  Lys  Thr
     370                      375                      380

ACG  CCT  CCC  GTG  CTG  GAC  TCC  GAC  GGC  TCC  TTC  TTC  CTC  TAC  AGC  AAG    1200
Thr  Pro  Pro  Val  Leu  Asp  Ser  Asp  Gly  Ser  Phe  Phe  Leu  Tyr  Ser  Lys
385                           390                 395                      400

CTC  ACC  GTG  GAC  AAG  AGC  AGG  TGG  CAG  CAG  GGG  AAC  GTC  TTC  TCA  TGC    1248
Leu  Thr  Val  Asp  Lys  Ser  Arg  Trp  Gln  Gln  Gly  Asn  Val  Phe  Ser  Cys
                    405                      410                      415

TCC  GTG  ATG  CAT  GAG  GCT  CTG  CAC  AAC  CAC  TAC  ACG  CAG  AAG  AGC  CTC    1296
Ser  Val  Met  His  Glu  Ala  Leu  His  Asn  His  Tyr  Thr  Gln  Lys  Ser  Leu
               420                      425                      430

TCC  CTG  TCT  CCG  GGT  AAA  TGA                                                 1317
Ser  Leu  Ser  Pro  Gly  Lys
                    435
```

( 2 ) INFORMATION FOR SEQ ID NO:11:

( i ) SEQUENCE CHARACTERISTICS:
        ( A ) LENGTH: 438 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Tyr  Val  Trp  Val  Gln  Gln  Pro  Thr  Ala  Leu  Leu  Leu  Leu  Gly  Leu
  1             5                      10                      15

Thr  Leu  Gly  Val  Thr  Ala  Arg  Arg  Leu  Asn  Cys  Val  Lys  His  Thr  Tyr
```

```
                        20                         25                           30
Pro  Ser  Gly  His  Lys  Cys  Cys  Arg  Glu  Cys  Gln  Pro  Gly  His  Gly  Met
          35                       40                      45

Val  Asn  Arg  Cys  Asp  His  Thr  Arg  Asp  Thr  Leu  Cys  His  Pro  Cys  Glu
          50                  55                      60

Thr  Gly  Phe  Tyr  Asn  Glu  Ala  Val  Asn  Tyr  Asp  Thr  Cys  Lys  Gln  Cys
65                       70                  75                            80

Thr  Gln  Cys  Asn  His  Arg  Ser  Gly  Ser  Glu  Leu  Lys  Gln  Asn  Cys  Thr
                    85                       90                       95

Pro  Thr  Gln  Asp  Thr  Val  Cys  Arg  Cys  Arg  Pro  Gly  Thr  Gln  Pro  Arg
               100                      105                 110

Gln  Asp  Ser  Gly  Tyr  Lys  Leu  Gly  Val  Asp  Cys  Val  Pro  Cys  Pro  Pro
          115                      120                      125

Gly  His  Phe  Ser  Pro  Gly  Asn  Asn  Gln  Ala  Cys  Lys  Pro  Trp  Thr  Asn
     130                      135                      140

Cys  Thr  Leu  Ser  Gly  Lys  Gln  Thr  Arg  His  Pro  Ala  Ser  Asp  Ser  Leu
145                      150                      155                      160

Asp  Ala  Val  Cys  Glu  Asp  Arg  Ser  Leu  Leu  Ala  Thr  Leu  Leu  Trp  Glu
               165                      170                      175

Thr  Gln  Arg  Pro  Thr  Phe  Arg  Pro  Thr  Thr  Val  Gln  Ser  Thr  Thr  Val
               180                      185                      190

Trp  Pro  Arg  Thr  Ser  Glu  Leu  Pro  Ser  Thr  Pro  Thr  Leu  Val  Glu  Pro
          195                      200                      205

Arg  Ser  Cys  Asp  Lys  Thr  His  Thr  Cys  Pro  Pro  Cys  Pro  Ala  Pro  Glu
          210                      215                      220

Ala  Glu  Gly  Ala  Pro  Ser  Val  Phe  Leu  Phe  Pro  Pro  Lys  Pro  Lys  Asp
225                      230                      235                      240

Thr  Leu  Met  Ile  Ser  Arg  Thr  Pro  Glu  Val  Thr  Cys  Val  Val  Val  Asp
                    245                      250                      255

Val  Ser  His  Glu  Asp  Pro  Glu  Val  Lys  Phe  Asn  Trp  Tyr  Val  Asp  Gly
               260                      265                      270

Val  Glu  Val  His  Asn  Ala  Lys  Thr  Lys  Pro  Arg  Glu  Glu  Gln  Tyr  Asn
          275                      280                      285

Ser  Thr  Tyr  Arg  Val  Val  Ser  Val  Leu  Thr  Val  Leu  His  Gln  Asp  Trp
     290                      295                      300

Leu  Asn  Gly  Lys  Glu  Tyr  Lys  Cys  Lys  Val  Ser  Asn  Lys  Ala  Leu  Pro
305                      310                      315                      320

Ala  Pro  Ile  Glu  Lys  Thr  Ile  Ser  Lys  Ala  Lys  Gly  Gln  Pro  Arg  Glu
               325                      330                      335

Pro  Gln  Val  Tyr  Thr  Leu  Pro  Pro  Ser  Arg  Asp  Glu  Leu  Thr  Lys  Asn
               340                      345                      350

Gln  Val  Ser  Leu  Thr  Cys  Leu  Val  Lys  Gly  Phe  Tyr  Pro  Ser  Asp  Ile
          355                      360                      365

Ala  Val  Glu  Trp  Glu  Ser  Asn  Gly  Gln  Pro  Glu  Asn  Asn  Tyr  Lys  Thr
     370                      375                      380

Thr  Pro  Pro  Val  Leu  Asp  Ser  Asp  Gly  Ser  Phe  Phe  Leu  Tyr  Ser  Lys
385                      390                      395                      400

Leu  Thr  Val  Asp  Lys  Ser  Arg  Trp  Gln  Gln  Gly  Asn  Val  Phe  Ser  Cys
               405                      410                      415

Ser  Val  Met  His  Glu  Ala  Leu  His  Asn  His  Tyr  Thr  Gln  Lys  Ser  Leu
               420                      425                      430

Ser  Leu  Ser  Pro  Gly  Lys
          435
```

( 2 ) INFORMATION FOR SEQ ID NO:12:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: Primer #

( x i ) SEQUENCE DESCRIPTION: SEQ ID NO:12:

GATCTTGGAA CGAGACGACC TGCT  24

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: Primer #

( x i ) SEQUENCE DESCRIPTION: SEQ ID NO:13:

AGCAGGTCGT CTCGTTCCAA  20

CYTOKINE WHICH IS A LIGAND FOR OX40

TECHNICAL FIELD OF THE INVENTION

The present invention relates to a novel cytokine. More specifically, the present invention relates to the cloning of a cytokine that binds to OX40.

BACKGROUND OF THE INVENTION

Cytokines are hormone-like factors that are active in regulating the survival, growth, differentiation and activity of various types of cells. Numerous cytokines have been described, and some of their functions elucidated. Several cytokines appear to be important in hematopoiesis, the process whereby pluripotent hematopoietic stem cells give rise to highly differentiated, mature blood cells that perform very specific functions (reviewed in Metcalf, D. 1984. *The Hemopoietic Colony Stimulating Factors.* Elsevier, Amsterdam, 486 pp). Cytokines designated "Interleukins" influence immune effector cells.

OX40 is a membrane glycoprotein with an approximate $M_r$ of 47–51 Kd that is present on the CD4+ subset of activated rate T cells (Paterson et al., *Mol. Immunol.* 24:1281; 1987). Mallett et al. (*EMBO J.* 9:1063, 1990) report the cloning and characterization of OX40, and the similarity of this membrane glycoprotein to the low affinity nerve growth factor receptor (NGFR). NGFR and OX40 are members of a superfamily of cell surface proteins defined by the presence of cysteine-rich motifs in the extracellular region (Mallett and Barclay, *Immunology Today* 12:220; 1991). This superfamily includes the B cell antigen CD40, the lymphocyte antigen CD27, CD30 (an antigen found on Hodgkin's lymphoma and Reed-Sternberg cells), two receptors for Tumor Necrosis Factor (TNF), a murine protein referred to as 4-1BB, and proteins encoded by the T2 open reading frame (ORF) of Shope fibroma virus (along with the equivalent proteins from other pox viruses) (Smith et al., *Biochem. Biophys. Res. Commun.* 176:335; 1991).

Prior to the present invention, a ligand for OX40 was unknown. Accordingly, there is a need in the art to identify and characterize an OX40 ligand (OX40-L).

SUMMARY OF THE INVENTION

The present invention comprises an isolated DNA molecule having a nucleotide sequence represented by nucleotides 148 through 741 of SEQ ID NO: 1, and their complements, which encodes a novel cytokine, OX40-L, that binds to a cell surface molecule referred to as OX40. The deduced amino acid sequence encoded by the novel DNA molecule is disclosed in SEQ ID NO: 1 and SEQ ID NO: 2. The present invention further comprises other DNA molecules that hybridize, under moderate or severe stringency conditions, to the DNA molecule defined by nucleotides 148 through 741 of SEQ ID NO: 1 and their complements. The invention further comprises DNA molecules which, due to the degeneracy of the genetic code, differ from the aforementioned DNA molecules but which encode polypeptides that bind OX40, and sequences complementary to them.

In addition, the present invention provides recombinant expression vectors comprising the inventive DNA molecules, and host cells transfected or transformed with the expression vectors. Methods of using the transformed or transfected host cells to produce recombinant proteins having OX40 binding activity are also provided.

The present invention further comprises OX40-L polypeptides, encoded by the inventive DNA molecules, which are capable of binding OX40. OX40-L is a type II membrane polypeptide having an extracellular region at its C-terminus, a transmembrane region and an intracellular region at its N-terminus. Soluble OX40-L comprises an extracellular region of OX40-L or a fragment thereof. The amino acid sequence of murine OX40-L is described in SEQ ID NO: 2. The extracellular region of murine OX40-L extends from amino acid 49 is amino acid 198 of SEQ ID NO: 2. OX40-L biological activity is mediated by binding of this cytokine with OX40 and includes co-stimulation of murine T cells (stimulation in the presence of suboptimal levels of a mitogen), and induction of Interleukin-2 (IL-2) and Interleukin-4 secretion (IL-4).

The present invention further provides antisense or sense oligonucleotides (deoxyribonucleotides or ribonucleotides) that correspond to a sequence of at least about 12 nucleotides selected from the nucleotide sequence of OX40-L, or DNA or RNA sequences complementary to the nucleotide sequence of OX40-L as described in SEQ ID NO: 1. Such antisense or sense oligonucleotides prevent transcription or translation of OX40-L mRNA or polypeptides.

Further still, the present invention provides OX40-L peptides fragments that correspond to a protein sequence of at least 10 amino acids selected from the amino acid sequence encoded by SEQ ID NO: 1 that can act as immunogens to generate antibodies specific to the OX40-L immunogens. Such OX40-L immunogen fragments can serve as antigenic determinants in providing monoclonal antibodies specific for OX40-L.

DETAILED DESCRIPTION OF THE INVENTION

Figure 1:
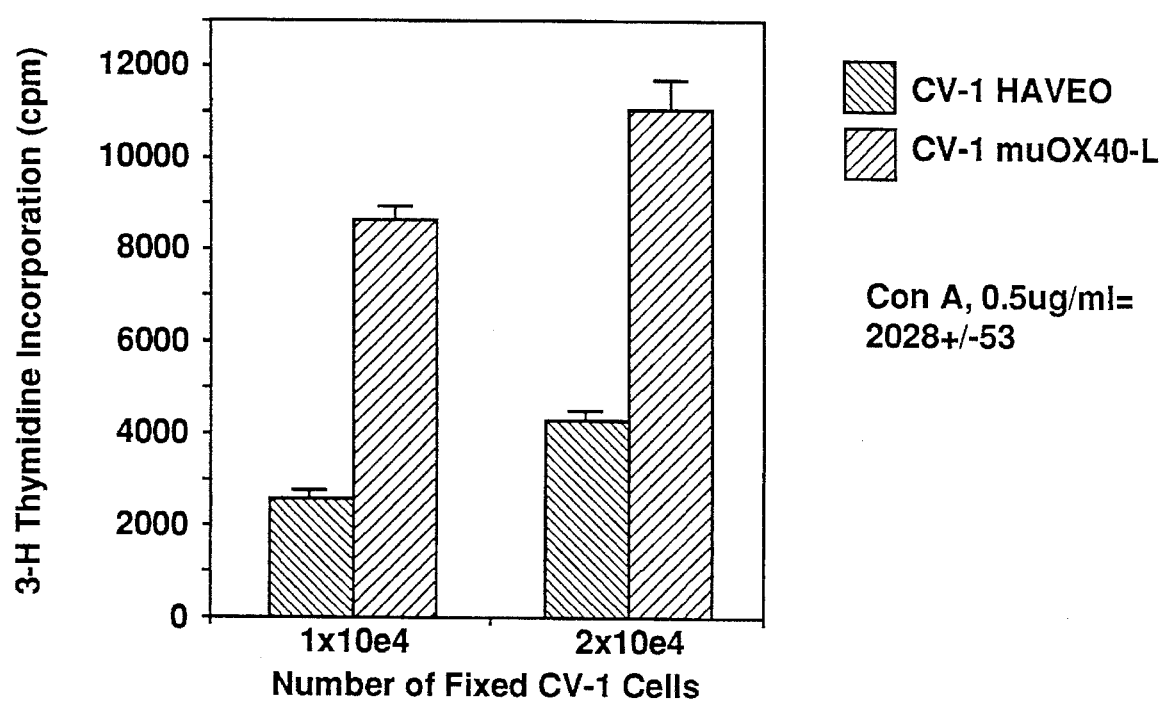
FIG. 1 illustrates the effect of fixed CV-1/EBNA cells transfected with an expression vector encoding mouse OX40-L versus fixed CV-1/EBNA cells transfected with vector alone on the proliferation of mouse T cells in the presence of a suboptimal level of mitogen (0.5 µg/l Concanavalin A).

A DNA molecule encoding a novel polypeptide that can act as a ligand for murine T cell antigen OX40 has been isolated and sequenced. More particular, the present invention comprises isolated DNA molecules encoding OX40-L selected from the group consisting of (a) nucleotides 148 through 741 of the nucleotide sequence set forth in SEQ ID NO: 1, and their complements, (b) DNA sequences which hybridize to the DNA sequences of (a) under conditions of moderate stringency and which encode an OX40-L polypeptide capable of binding OX40, and (c) DNA sequences which, due to the degeneracy of the genetic code, encode OX40-L polypeptides encoded by any of the foregoing DNA sequences, and their complements. In addition, the present invention includes expression vectors comprising DNA sequences encoding OX40-L polypeptides, and host cells transfected or transformed with such vectors. Further provided are methods of using the transfected or transformed host cells to express recombinant OX40-L polypeptides.

OX40-L polypeptides include other forms of mammalian OX40-L, such as derivatives or analogs of murine OX40-L, and mammalian homologs of murine OX40-L. Murine OX40-L comprise a 150 amino acid extracellular region at the C-terminus of full length, membrane-bound polypeptide. The extracellular region contains the domain that binds to OX40. Murine OX40-L further comprises a putative hydrophobic 20 amino acid transmembrane region delineated by charged amino acids on either side and a 28 amino acid intracellular region at the N-terminus. The present invention further comprises a full length OX40-L polypeptides, or fragments there comprising all or part of the extracellular region.

Full-length OX40-L is a type II polypeptide having its N-terminus as its intracellular domain, followed by a transmembrane region, and an extracellular domain at the C-terminus of the polypeptide. The extracellular domain, which is longer than either the intracellular domain or the transmembrane region, contains one potential N-linked glycosylation site and two potential disulfide bonds in view of four cysteine (Cys) residues in the extracellular region. A soluble version of OX40-L can be made from the extracellular region or a fragment thereof. The extracellular region of murine OX40-L extends from amino acid 49 to amino acid 198 of SEQ ID NOs: 1 and 2.

The novel cytokine disclosed herein is a ligand for OX40, a receptor that is a member of the TNF receptor super family. Therefore, OX40-L is likely to be responsible for transducing signal via OX40, which is known to be expressed, for example, by T lymphocytes. The biological activity of OX40-L is mediated by binding to OX40 or a species-specific homolog thereof and comprises stimulation of T cells in the presence of sub-optimal levels of a mitogen such as Concanvalin A (Con A) or phytohemagglutinin (PHA). OX40-L also acts as a potent co-stimulus in the induction of IL-2 and IL-4 secretion, and is useful in culturing primary T cells for development of clonal T cell lines.

The nucleotide sequence of the coding region of the DNA encoding OX40-L exhibits 73% similarity to a nucleotide sequence from a coding region of a DNA encoding a protein designated gp34 (Miura et al., *Mol Cell. Biol.* 11:1313; 1991), using the BESTFIT program (University of Wisconsin Genetics Computer Group, Madison, Wis., (USA). gp34 is a glyucoprotein expressed in cells infected with human T-cell leukemia virus type I (HTLV-I); according to BEST-FIt analysis, OX40-L and gp34 are 62% similar on the amino acid level.

Nucleic acid molecules within the scope of the present invention include DNA and/or RNA molecules that hybridize to the DNA molecule represented by SEQ ID NO: 1 and its complementary strand, under conditions of moderate or severe stringency, and which encode OX40-L polypeptides that are capable of binding OX40. Moderate stringency hybridization conditions refer to conditions described in, for example, Sambrook et al. *Molecular Cloning: A Laboratory Manual,* 2 ed. Vol. 1, pp. 1.101–104, Cold Spring Harbor Laboratory Pres, (1989). Conditions of moderate stringecy, as defined by Sambrook et al., include use of a prewashing solution of 5 X SSC, 0.5% SDS, 1.0 mM EDTA (pH 8.0) and hybridization conditions of 50° C., 5 X SSC, overnight. Conditions of severe stringency include higher temperatures of hybridization and washing. Such hybridizing DNA molecules differ from the DNA molecule represented by SEQ ID NO: 1 because of one or a plurality of deletions, insertions or substitutions of nucleotides, and can be prepared by oligonucleotide synthesis and ligation or by site-specific mutangenesis techniques.

OX40-L refers to a genus of polypeptides which are capable of binding OX40, or mammalian homologs of OX40. As used herein, the term "OX40-L" includes soluble OX40-L polypeptides lacking transmembrane and intracellular regions, mammalian homologs of OX40-L, analogs OX40-L or derivatives of OX40-L. OX40-L may also be obtained by mutations of nucleotide sequences coding for an OX40-L polypeptide. An OX40-L analog, as referred to herein, is a polypeptide encoded by a DNA molecule capable of hybridizing to the DNA molecule represented by SEQ ID NO: 1 under conditions of moderate stringency.

The primary amino acid structure of human or murine OX40-L may be modified to create OX40-L derivatives by forming covalent or aggregative conjugates with other chemical moieties, such as glycosyl groups, lipids, phosphate, acetyl groups and the like, or by creating amino acid sequence mutants. Covalent derivatives of OX40-L are prepared by linking particular functional groups to OX40-L amino acid side chains or at the N-terminus or C-terminus of a OX40-L polypeptide or the extracellular domain thereof, or to carbohydrate moieties present on OX40-L polypeptides.

Other OX40-L polypeptides within the scope of this invention include covalent or aggregative conjugates of OX40-L or its fragments with other proteins or polypeptides, such as by synthesis in recombinant culture as N-terminal or C-terminal fusions. For example, the conjugate may comprise a signal or leader polypeptide sequence at the N-terminal region or C-terminal region of a OX40-L polypeptide which co-translationally or post-translationally directs transfer of the conjugate from its site of synthesis to a site inside or outside of the cell membrane or cell wall (e.g. a human or murine Interleukin-7 leader sequence, or an α-factor of Saccharomyces). OX40-L polypeptide fusions can comprise polypeptides added to facilitate purification and identification of OX40-L (e.g. poly-His), or fusions with other cytokines to provide novel polyfunctional entities. Other cytokines include, for example, any of the interleukins, TNF (tumor necrosis factor), GM-CSF (granulocyte macrophage-colony stimulating factor), G-CSF (granulocyte-colony stimulating factor), MGF (mast cell growth factor), EGF (epidermal growth factor), PDGF (platelet-derived growth factor), NGF (nerve growth factor), EPO (erythropoietin, γ-IFN (gamma interferon), 4-1BB-L (4-1BB ligand) and other cytokines that affect immune cell growth, differentiation or function.

Biological activity of OX40-L may be determined, for example, by competition for binding to the ligand binding domain of OX40 (i.e. competitive binding assays). One configuration of a competitive binding assay for OX40-L polypeptide uses a radiolabeled, soluble murine OX40-L according to SEQ ID NO: 1, and intact cells expressing OX40 (e.g., activated murine $CD4^+$ T cells). Instead of intact cells, one could substitute soluble OX40 (such as a OX40Fc fusion protein) bound to a solid phase through a Protein A or Protein G interaction with the Fc region of the fusion protein. A second configuration of a competitive binding assay utilizes radiolabeled soluble OX40 such as an OX40/Fc fusion protein, and intact cells expression OX40-L. Alternatively, soluble OX40-L could be bound to a solid phase.

Competitive binding assays can be performed using standard methodology. For example, radiolabeled murine OX40-L can be used to compete with a putative OX40-L homolog to assay for binding activity against surface-bound OX40. Qualitative results can be obtained by competitive autoradiographic plate binding assays, or fluorescence activated cell sorting, or Scatchard plots may be utilized to generate quantitative results.

Competitive binding assays with intact cells expressions OX40 can be performed by two methods. In a first method, $CD4^+$ T cells are grown are cultured and activated according to standard methodology (for example, as described in Grabstein et al., *J. Immunol.* 150:3141, 1993). In a second method, transfected cells expressing full length, membrane-bound OX40 with an extracellular region exterior to the cell can be used.

Alternatively, soluble OX40 can be bound to a solid phase such as a column chromatography matrix, or a tube or similar substrate suitable for analysis for the presence of a detectable moiety such as $^{125}I$. Binding to a solid phase can be accomplished, for example, by obtaining a OX40/Fc fusion protein and binding it to a protein A or protein G surface.

Another means to measure the biological activity of OX40-L and homologs thereof is to utilize conjugated, soluble OX40 (for example, $^{125}I$-OX40/Fc) in competition assays similar to those described above. In this case, however, intact cells expressing OX40-L, or soluble OX40-L bound to a solid substrate, are used to measure competition for binding of conjugated, soluble OX40 to OX40-L by a sample containing a putative OX40 homolog.

OX40-L may also be assayed by measuring biological activity in a T cell proliferation assay. Briefly, purified T cells are obtained by methods that are known in the art. The purified T cells are incubated in the presence of membrane-bound OX40-L and a suboptimal level of a mitogen such as Con A or PHA. Proliferation is determined by measuring the incorporation of a radiolabeled substance such as $^3H$ thymidine according to standard methods.

Yet another assay for determining OX40-L biological activity is induction of the secretion of IL-2 and IL-4 by T cells. T cells are purified and stimulated with OX40-L in the presence of a suboptimal level of a mitogen as described previously. Induction of IL-2 secretion is determined by bioassay, measuring the proliferation of an IL-2 dependent cell line. Similarly, induction of IL-4 secretion is determined by measuring the proliferation of an IL-4 dependent cell lines.

OX40-L can be used in a binding assay to detect cells expression OX40 or homologs thereof. For example, murine OX40-L according to SEQ ID NO: 1, or an extracellular domain or a fragment thereof, can be conjugated to a detectable moiety such as $^{125}I$. Radiolabeling with $^{125}I$ can be performed by any of several standard methodologies that yield a functional $^{125}I$-OX40-L molecule labeled to high specific activity. Alternatively, another detectable moiety such as an enzyme that can catalyze a colorimetric or fluorometric reaction, biotin or avidin may be used. The conjugated OX40-L is diluted into a suitable medium. Cells expressing OX40 or an OX40 homolog are incubated with the medium containing the conjugated OX40-L. After incubation, unbound conjugated OX40-L is removed and binding is measured using the detectable moiety.

OX40-L polypeptides may exist as oligomers, such as dimers or trimers. Oligomers may be linked by disulfide bonds formed between cysteine residues on different OX40-L polypeptides. Alternatively, one can link two soluble OX40-L domains with a linker sequence, such as those described in U.S. Pat. No. 5,073,627, which is incorporated by reference herein. OX40-L polypeptides may also be created by fusion of the C terminal of soluble OX40-L (extracellular domain) to the Fc region of IgG1 (for example, as described in Fanslow et al., *J. Immunol.* 149:655; 1992). OX40-L/Fc fusion proteins are allowed to assemble much like heavy chains of an antibody molecule to form divalent OX40-L. If fusion proteins are made with both heavy and light chains of an antibody, it is possible to form an OX40-L oligomer with as many as four OX40-L extracellular regions. Alternatively, oligomeric OX40-L proteins may be created by fusion of the C terminal domain of OX40 with a leucine zipper peptide that spontaneously oligomerizes in solution, as described in U.S. Ser. No. 07/969,703, filed Oct. 23, 1992, the disclosure of which is hereby incorporated by reference.

Fusion proteins can be prepared using conventional techniques of enzyme cutting and ligation of fragments from desired sequences. PCR techniques employing synthetic oligonucleotides may be used to prepare and/or amplify the desired fragments. Overlapping synthetic oligonucleotides representing the desired sequences can also be used to prepare DNA constructs encoding fusion proteins. Fusion proteins can also comprise OX40-L and two or more additional sequences, including a leader (or signal peptide) sequence, Fc region, linker sequence, a leucine zipper sequence, and sequences encoding highly antigenic moieties that provide a means for facile purification or rapid detection of a fusion protein.

Signal peptides facilitate secretion of proteins from cells. An exemplary signal peptide is the amino terminal 25 amino acids of the leader sequence of murine interleukin-7 (IL-7; Namen et al., *Nature* 333:571; 1988). Other signal peptides may also be employed furthermore, certain nucleotides in the IL-7 leader sequence can be altered without altering the amino acid sequence. Additionally, amino acid changes that do not affect the ability of the IL-7 sequence to act as a leader sequence can be made.

The Flag® octapeptide (Asp-Tyr-Lys-Asp-Asp-Asp-Asp-Lys) does not alter the biological activity of fusion proteins, is highly antigenic and provides an epitope reversibly bound by a specific monoclonal antibody, enabling rapid detection and facile purification of the expressed fusion protein. The Flag® sequence is also specifically cleaved by bovine mucosal enterokinase at the residue immediately following the Asp-Lys pairing. Fusion proteins capped with this peptide may also be resistant to intracellular degradation in *E. coli*. A murine monoclonal antibody that binds the Flag® sequence has been deposited with the ATCC under accession number HB9259; methods of using the antibody in purification of fusion proteins comprising the Flag® sequence are described in U.S. Pat. No. 5,011,912, which is incorporated by reference herein.

Suitable Fc regions are defined as Fc regions that can bind to protein A or protein G, or alternatively, are recognized by an antibody that can be used in purification or detection of a fusion protein comprising the Fc region. Preferable Fc regions include the Fc region of human $IgG_1$ or murine IgG₁. One example is the human IgG₁ Fc mutein shown in SEQ ID NOs: 10 and 11; another example is an Fc region encoded by cDNA obtained by PCR as described by Fanslow et al., *J. Immunol.* 149:65 (1992). Portions of a suitable Fc region may also be used, for example, an Fc region of human IgG₁ from which has been deleted a sequence of amino acids responsible for binding to protein A, such that the results Fc region binds to protein G but not protein A.

OX40-L may be linked directed to another protein to form a fusion protein; alternatively, the OX40-L and the other protein may be separated by a distance sufficient to ensure that the OX40-L properly folds into its secondary and tertiary structures. Suitable linker sequences (1) will adopt a flexible extended conformation, (2) will not exhibit a propensity for developing an ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions which can be used to separate the functional domains and prevent steric interference. Exemplary linker sequences are described in U.S. Pat. Nos. 5,073,627 and 5,108,910, the disclosure of which are hereby incorporated by reference.

OX40-L polypeptides may exist as soluble polypeptides comprising the extracellular domain of OX40-L as shown in SEQ ID NOs: 1 and 2, amino acids 49 through 198, or as membrane-bound polypeptides comprising the extracellular domain, a transmembrane region and a short intracellular domain, as shown in SEQ ID NOs: 1 and 2, amino acids 1 through 198. Moreover, the present invention comprises oligomers of OX40-L extracellular domains or fragments thereof, linked by disulfide interactions, or expressed as fusion polymers with or without spacer amino acid linking groups. For example, a dimer OX40-L molecule can be linked by an IgG Fc region linking group.

The ability of OX40-L to co-stimulate T cell proliferation and cytokine secretion suggests a role for OX40-L as an autocrine growth ligand in T cell activation. Furthermore, native OX40-L is a plasma membrane protein, and may be involved in direct cell-dependent interactions between T cells. Thus, the OX40/OX40-L interaction may comprise a component of the adhesion of T cells to one another that is seen following activation with antigen or mitogen. Moreover, the stimulation of IL-2 and IL-4 secretion suggests that OX40-L has its effect upon the TH0 and/or TH2 subpopulations of T cells (Mosmann and Coffman, *Immunol, Today* 8:223, 1987; Mosmann and Coffman, *Adv. Immunol.* 46:111, 1988). It is known in the art that generation of TH2 versus TH1 populations of T cells will have an effect upon the type and effectiveness of the ensuing immune response (Coffman et al., *Immuno. Rev.* 123:189; 1991). The ability of OX40-L to induce both IL-2 and IL-4 indicates that OX40-L has the potential to modify a number of immune responses, including the nature of the immunoglobulin isotype generated and the development of cytolytic T cells. Therefore, OX40-L is likely to be useful in inducing a TH2 immune response, for example as a vaccine adjuvant, or in ex vivo techniques to stimulate selected populations of TH2 cells. An OX40-L antagonist may similarly be useful in directing an immune response toward a TH1 response or in inhibiting TH2 responses. OX40-L will also be useful as an in vitro reagent for the culture of primary T cells and the development of clonal T cells lines, or for the detection of cells expression OX40 or an OX40 homolog.

The present invention further includes OX40-L polypeptides with or without associated native-pattern glycosylation. OX40-L expressed in yeast or mammalian expression systems (e.g., COS-7 cells) may be similar to or significantly different from a native OX40-L polypeptide in molecular weight and glycosylation pattern, depending upon the choice of expression system. Expression of OX40-L polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding can be prepared. For example, the extracellular OX40-L N-glycosylation site at amino acid residues 91–93 can be modified to preclude glycosylation while allowing expression of a homogeneous, reduced carbohydrate analog using yeast expression systems. N-glycosylation sites in eukaryotic polypeptides are characterized by an amino acid triplet Asn-X-Y, wherein X is any amino acid except Pro and Y is Ser or Thr. Appropriate modifications to the nucleotide sequence encoding this triplet will result in substitutions, additions or deletions that prevent attachment of carbohydrate residues at the Asn side chain.

In another example, sequences encoding Cys residues can be altered to cause the Cys residues to be deleted or replaced with other amino acids, preventing formation of incorrect intramolecular disulfide bridges upon renaturation. Human OX40-L comprises four Cys residues in its extracellular domain, and two Cys residues within the putative transmembrane region. One or more of the Cys residues in the transmembrane region can be replaced with another amino acid or deleted without affecting protein tertiary structure or disulfide bond formation.

Furthermore, nucleotides encoding the intracellular region and transmembrane region of OX40-L may be deleted, resulting in a soluble OX40-L. Nucleotides encoding additional amino acids may be deleted from the ends of a DNA encoding the extracellular region of OX40-L, resulting in truncated forms of soluble OX40-L. For example, a DNA encoding a polypeptide defined by a sequence beginning with an amino acid in the sequence between amino acid 49 and amino acid 69, inclusive, through and including an amino acid in the sequence between amino acid 164 and amino acid 198, inclusive, of the sequence set forth in SEQ ID NO: 2 can be prepared. Such a DNA will still encode an OX40-L polypeptide having the four Cys residues present in the extracellular region of native OX40-L. DNAs encoding soluble OX40-L may further comprise nucleotides encoding signal peptides, linker sequences, peptides that facilitate purification or peptides that allow oligomerization, as described herein.

Other approaches to mutagenesis involve modification of sequences encoding dibasic amino acid residues to enhance expression in yeast systems in which KEX2 protease activity is present. Sub-units of a OX40-L polypeptide may be constructed by deleting sequences encoding terminal or internal residues or sequences.

OX40-L polypeptides are encoded by multi-exon genes. The present invention further includes alternative mRNA constructs which can be attributed to different mRNA splicing events following transcription and which share regions of identity or similarity with the cDNAs disclosed herein.

Antisense or sense oligonucleotides comprise a single-stranded nucleic acid sequence (either RNA or DNA) capable of binding to target OX40-L sequences. Antisense or sense oligonucleotides, according to the present invention, comprise a fragment of SEQ ID NO: 1, or a DNA or RNA complement of SEQ ID NO: 1 which comprises at least about 14 nucleotides. Preferably, such a fragment comprises from about 14 to about 30 nucleotides. The ability to create an antisense or a sense oligonucleotide, based upon a cDNA sequence for OX40-L is described in, for example, Stein and Cohen, *Cancer Res.* 48:2659, 1988 and van der Krol et al., *BioTechniques* 6:958, 1988. Binding of antisense or sense oligonucleotides to target nucleic acid sequences results in the formation of complexes that block translation (RNA) or transcription (DNA) by one of several means, including enhanced degradation of the complexes, premature termination of transcription or translation, or by other means.

Antisense or sense oligonucleotides further comprise oligonucleotides having modified sugar-phosphodiester backbones that are resistant to endogenous nucleases (described in WO91/06629), or which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense onconuleotides may be introduced into a cell containing the target nucleic acid sequence by any gene transfer method, including, for example, $CaPO_4$-mediated DNA transfection, electroportion, or gene transfer vectors such as Epstein-Barr virus or suitable retroviral vectors such as those described in PCT application U.S. No. 90/02656. Sense or antisense oligonucleotides may also be introduced into a cell containing the target nucleotide sequence by formation of a conjugate with a ligand binding molecule (for example, cell surface receptors, growth factors, cytokines, or other ligands that bind to cell surface receptors), as described in WO 91/04753. Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The sequence of murine OX40-L cDNA was obtained by direct expression techniques by first obtaining a clone of the extracellular region of mouse OX40 (the receptor) by polymerase chain reaction (PCR) techniques using primers based upon a sequence for rat OX40 published in Mallett et al., *EMBO J.* 9:1063 (1990). The sequence of the extracellular domain of the mouse OX40 cloned by this method is shown in SEQ ID NOs: 6 and 7. The upstream oligonucleotide (represented by SEQ ID NO: 3) comprises a recognition site for the restriction endonuclease Spe I (nucleotides 3–8) upstream of a sequence encoding the first six (N-terminal) amino acids of OX40 (nucleotides 13–30). The downstream oligonucleotide (represented by SEQ ID NO: 4) comprises a recognition site for the restriction endonuclease Spe I (nucleotides 3–8) upstream of a sequence encoding the last five (C-terminal) amino acids of OX40 (nucleotides 10–24).

The PCR product was digested with Spe I, and an approximately 800 bp fragment was isolated by gel filtration, and used in a second round of PCR reaction. The isolated fragment was ligated into Spe I cut plasmid, pBLUESCRIPT SK® (Stratagene Cloning Systems, La Jolla, Calif.), which was used to PCR an extracellular region of murine OX40 using the oligionucleotide primers represented in SEQ ID NO: 3 and SEQ ID NO: 5. The oligonucleotide defined by SEQ ID NO: 5 deletes the C-terminal five amino acids of the region of murine OX40 that corresponds to the extracellular region of rat OX40 as described by Mallett et al., and includes a Bgl II site, and a sequence encoding two amino acids from the N-terminal of an Fc region of a human $IgG_1$.

The PCR product was used in a three-way ligation of the murine OX40 extracellular region and DNA encoding a human IgG Fc (as described in U.S. Ser. No. 07/969,703) into Sal I/Not I cut pBLUESCRIPT SK®. After amplification in *E. coli*, the insert encoding the OX40Fc fusion protein was digested with Sal I/Not I, and cloned into plasmid pDC406 (McMahan et al., *EMBO J.* 10:2821, 1991). Site-directed mutageneis, essentially as described by Deng and Nickoloff, *Anal. Biochem.* 200:81 (1992) was used to change three amino acid residues in the Fc region (Leu234 to Ala, Leu235 to Glu and Gly237 to Ala, using the amino acid numbering of Canfield and Morrison, *J. Exp. Med.* 173:1483; 1991). The resulting OX40/Fc mutein exhibited reduced affinity for immunoglobulin receptors.

Other fusion proteins comprising ligand binding domains from other receptors can be made by obtaining a DNA sequence for the ligand binding domain of a receptor and fusing this sequence to a DNA sequence encoding an Fc region of an antibody molecule that binds to protein A or protein G, or another polypeptide that is capable of affinity purification, for example, avidin or streptavidin. The resultant gene construct can be introduced into mammalian cells to transiently express a fusion protein. Receptor/Fc fusion proteins can be purified by protein A or protein G affinity purification. Receptor/avidin fusion proteins can be purified by biotin affinity chromatography. The fusion protein can later be removed from the column by eluting with a high salt solution or another appropriate buffer.

Receptor/Fc fusion molecules preferably are synthesized in recombinant mammalian cell culture because they are generally too large and complex to be synthesized by prokaryotic expression methods. Examples of suitable mammalian cells for expressing a receptor/Fc fusin protein include CV-1 cells (ATCC CRL 70), COS-7 cells (ATCC CRL 1651), both derived from monkey kidney, and CV-1/EBNA cells (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter. An EBNA-1 gene allows for episomal replication of expression vectors, such as pDC406, that contain the EBV origin of replication.

Large scale cultures of transfected cells were grown to accumulate supernatant from cells expressing OX40/Fc mutein. OX40Fc mutein in supernatant fluid was purified by affinity purification using a protein A antibody affinity column (BioRad, Richmond, Calif, USA). The nucleotide and amino acid sequence of OX40/Fc mutein are shown in SEQ ID NOs: 10 and 11. Several cell lines were screened using OX40/Fc mutein and FITC-labeled goat anti-human IgG antibody by flow cytometry. A clonal cell line, S49.1 (ATCC TIB 128), a murine T cell lymphoma line was found to express approximately 1,000 molecules of putative OX40-L per cell.

A cDNA expression library was made essentially as described in U.S. Pat. No. 4,968,6507, from PMA-stimulated S49.1 cells. Briefly, cDNA was synthesized, inserted into empty pDC410 vector (a derivative of pDC406 (McMahan et al. *EMBO J.* 10:2821, 1991) with a unique Bgl II site and bearing the SV40 T antigen gene) and transformed into *E. coli*. Transformants were pooled, and the DNA from the pools was isolated and transfected into CV-1/EBNA cells to create an expression cloning library. Transfected CV-1/EBNA cells were cultured to permit transient expression of OX40-L. The transfected cells were then incubated with OX40/Fc mutein, followed by radio-iodinated murine anti-human IgG Fc (F(ab)$_2$, with wash steps to remove non-specifically bound material, and fixed with gluteraldehyde. The fixed slides were dipped in liquid photographic emulsion and exposed in the dark. After developing the slides, they were individually examined with a miscroscope and cells expressing OX40-L were identified by the presence of dark autoradiographic silver grains against a light background.

The expression cloning library was screened and four pools, containing approximately 2000 individual clones, were identified as positive for binding OX40/Fc mutein. One pool was broken down into smaller pools of approximately 250 colonies. The smaller pools were screened as described above. One of the smaller pools was positive for OX40-L.

A first clone was isolated and sequenced by standard techniques, to provide the cDNA sequence and deduced amino acid sequence of murine OX40-L. Sequencing results indicated an open reading fame upstream of the putative initiator methionine. A second, longer clone was isolated by screening colonies from the sub-pools by colony hybridization with a radioactive OX40-L probe, generated from the first clone. The cDNA insert in the longer clone was extended by 110 bp in the 5' region of the OX40-L cDNA. The nucleotide and deduced amino acid sequence of the second, longer clone are shown in SEQ ID NOS: 1 and 2.

One can utilize the murine OX40-L cDNA sequences disclosed herein to obtain cDNAs encoding other mammalian homologs of murine OX40-L by cross-species hybridization techniques. Briefly, an oligonucleotide probe is created from the nucleotide sequence of the extracellular region of murine OX40-L as shown in SEQ ID NO: 1. This probe can be made by standard techniques, such as those described in Maniatis et al., *Molecular Biology: A Laboratory Manual,* Cold Spring Harbor Laboratory, N.Y., 1982, pages 316–328. The murine probe is used to screen a mammalian cDNA library or genomic library under moderate stringency conditions. Examples of mammalian cDNA or genomic libraries include, for cDNA, a library made from the mammal's peripheral blood lymphocytes. Alternatively, various cDNA libraries or mRNAs isolated from various cell lines can be screened by Northern hybridization to determine a suitable source of mammalian OX40-L DNA or mRNA.

Recombinant expression vectors for expression of OX40-L by recombinant DNA techniques include a OX40-L DNA sequence comprising a synthetic or cDNA-derived DNA fragment encoding a OX40-L polypeptide, operably linked to a suitable transcriptional or translational regulatory nucleotide sequence, such as one derived from a mammalian, microbial, viral, or insect gene. Examples of regulatory sequences include sequences having a regulatory role in gene expression (e.g., a transcriptional promoter or enhancer), optionally an operator sequence to control transcription, a sequence encoding an mRNA ribosomal binding site, and appropriate sequences which control transcription and translation initiation and termination. Nucleotide sequences are operably linked when the regulatory sequence functionally relates to the OX40-L DNA sequence. Thus, a promoter nucleotide sequence is operably linked to a OX40-L DNA sequence if the promoter nucleotide sequence controls the transcription of the OX40-L DNA sequence. Still further, a ribosome binding site may be operably linked to a sequence for a OX40-L polypeptide if the ribosome binding site is positioned within the vector to encourage translation. In addition, sequences encoding signal peptides can be incorporated into expression vectors. For example, a DNA sequence for a signal peptide (secretory leader) may be operably linked to a OX40-L DNA sequence. The signal peptide is expressed as a precursor amino acid sequence which enables improved intracellular secretion of translated fusion polypeptide by a yeast host cell. An exemplary vector is pDC406, which includes regulatory sequences derived from SV40, human immunodeficiency virus (HIV), and Epstein-Barr virus (EBV).

Suitable host cells for expression of OX40-L polypeptides include prokaryotes, yeast or higher eukaryotic cells. Prokaryotes include gram negative or gram positive organisms, for example, *E. coli* or Bacilli. Suitable prokaryotic host cells for transformation include, for example, *E. coli, Bacillus subtilis, Salmonella typhinurium,* and various other species with the genera Pseudomonas, Streptomyces, and Staphylococcus. Higher eukaryotic cells include established cell lines of mammalian origin. Cell-free translation systems could also be employed to produce OX40-L polypeptides using RNAs derived from DNA constructs disclosed herein. Appropriate cloning and expression vectors for use with bacterial, fungal, yeast and mammalian cellular hosts are described, for example, in Pouwels et al. *Cloning Vectors: A Laboratory Manual,* Elsevier, N.Y., (1985).

In a prokaryotic host cell, such as *E. coli,* an OX40-L polypeptide or analog may include an N-terminal methionine residue to facilitate expression of the recombinant polypeptide in the prokaryotic host cell. The N-terminal Met may be cleaved from the expressed recombinant OX40-L polypeptide. Prokaryotic host cells may be used for expression of OX40-L polypeptides that do not require extensive proteolytic or disulfide processing.

The expression vectors carrying the recombinant OX40-L DNA sequence are transfected or transformed into a substantially homogeneous culture of a suitable host microorganism or mammalian cell line. Transformed host cells are cells which have been transformed or transfected with nucloetide sequences encoding OX40-L polypeptides and express OX40-L polypeptides. Expressed OX40-L polypeptides will be located within the host cell and/or secreted into culture supernatant fluid, depending upon the nature of the host cell and the gene construct inserted into the host cell.

Expression vectors transfected into prokaryotic host cells generally comprise one or more phenotypic selectable markers. A phenotypic selectable marker is, for example, a gene encoding a protein that confers antibiotic resistance or that supplies an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a OX40-L DNA sequence. Other commercially vectors include, for example, pKK223-3 (Pharmacia Fine Chemicals, Uppsala, Sweden) and pGEM1 (Promega Biotec, Madison, Wis. USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

OX40-L may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657.

Yeast vectors can be assembled, for example, using DNA sequences from pBR322 for selection and replication in *E. coli* ($Amp^r$ gene and origin of replication). Other yeast DNA sequences that can be included in a yeast expression construct include a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See e.g., Kurjan et al., *Cell* 30:933, 1982 and Bitter et al., *Proc. Natl. Acad. Sci.* USA 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Sci.* USA 75:1929, 1978. for example, one can select for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant OX40-L polypeptides. Examples of suitable mammalian host cell lines include the COS-7 line of monkey kidney cells (ATCC CRL 1651; Gluzman et al., *Cell* 23:175, 1981), L cells, C127 cells, 3T3 cells (ATCC CCL 163), Chinese Hamster ovary (CHO) cells, HeLa cells, and BHK (ATCC CRl 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional terminal sequences.

Transcriptional and translational control sequences for mammalian host cell expression vectors may be excised from viral genomes. For example, commonly used mammalian cell promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, now abandoned, incorporated by reference herein. For expression of a type II protein extracellular region, such as OX40-L, a heterologous signal sequence may be added, such as the signal sequence for interleukin-7 (IL-7) described in U.S. Pat. No. 4,965,195, or the signal sequence for interleukin-2 receptor described in U.S. patent applicaton No. 06/626,667, filed on Jul. 2, 1984, now abandoned.

Human or murine OX40-L can be made in membrane-bound form when an intracellular and transmembrane regions are included or in soluble form with only the extracellular domain. CV1/EBNA cells were transfected with a cDNA shown in SEQ ID NO: 1 in pDC406 to yield transfected cells expressing membrane-bound murine OX40-L.

Purification of Recombinant OX40-L Polypeptides

OX40-L polypeptides may be prepared by culturing transformed host cells under culture conditions necessary to express OX40-L polypeptides. The resulting expressed polypeptides may then be purified from culture media or cell extracts. A OX40-L polypeptide, if desired, may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reverse-phase high performance liquid chromatography (RP-HPLC) steps employing hydrophobic RH-HPLC media, (e.g., silica gel having pendant methyl or other aliphatic groups) can be employed to further purify OX40-L. Some or all of the foregoing purification steps, in various combinations, can also be employed to provide a substantially homogeneous recombinant protein.

It is also possible to utilize an affinity column comprising OX40 ligand binding domain to affinity-purify expressed OX40-L polypeptides. OX40-L polypeptides can be removed from an affinity column in a high salt elution buffer and then dialyzed into a lower salt buffer for use.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express OX40-L as a secreted polypeptide. This simplifies purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Administration of OX40-L Compositions

The present invention provides therapeutic compositions comprising an effective amount of OX40-L in a suitable diluent or carrier and methods of treating mammals using the compositions. For therapeutic use, purified OX40-L or a biologically active analog thereof is administered to a patient, preferably a human, for treatment in a manner appropriate to the indication. Thus, for example, OX40-L pharmaceutical compositions (for example, in the form of a soluble extracellular domain, or a fragment thereof) which is administered to achieve a desired therapeutic effect can be given by bolus injection, continuous infusion, sustained release from implants, or other suitable technique. Typically, a OX40-L therapeutic agent will be administered in the form of a pharmaceutical composition comprising purified OX40-L polypeptide in conjunction with physiologicaly acceptable carriers, excipients or diluents. Such carriers will be nontoxic to patients at the dosages and concentrations employed. Ordinarily, the preparation of such compositions entails combining a OX40-L polypeptide with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents. OX40-L sense or antisense oligonucleotides may be administered in vivo by administering an effective amount of a vector containing a nucleic acid sequence that encodes and effective antisense or sense oligonucleotide. Additionally, OX40-L sense or antisense oligonucleotides may be administered ex vivo by removing cells containing OX40-L DNA or mRNA from an individual, incorporating an antisense or sense oligonucleotide into the cells using gene transfer techniques, and re-infusing the cells into the individual.

The following examples are intended to illustrate particular embodiments and not limit the scope of the invention.

EXAMPLE 1

This example described construction of an OX40/Fc DNA construct to express a soluble OX40Fc fusion protein. The cDNA sequence of the extracellular region or ligand binding domain of complete murine OX40 receptor sequence was obtained using polymerase chain reaction (PCR) techniques, and is based upon the rat sequence published in Mallett et al., *EMBO J.* 9:1063 (1990), supra. Total RNA was obtained from murine T cell clone 7B9 (Mosley et al., *Cell* 59:335; 1989) which had been stimulated with concanavalin A for 26 hours. A first strand cDNA was prepared from oligo dT-primed RNA using a commercially available kit (SuperScript™ cDNA kit; GIBCO/BRL, Gaithersburg, Md.)

A PCR technique (Saiki et al., *Science* 239:487, 1988) was employed using 5' (upstream) and 3' (downstream) oligonucleotide primers to amplify the DNA sequences encoding full length OX40 (SEQ ID Nos: 3 and 4, respectively). SEQ ID NO: 3 comprises a recognition site for the restriction endonuclease Spe I (nucleotides 4–9) upstream of a sequence encoding the first six (N-terminal) amino acids of OX40 (nucleotides 14–31). SEQ ID NO: 4 comprises a recognition site for the restriction endonuclease Spe I (Nucleotides 4–9) upstream of a sequence encoding the last five (C-terminal) amino acids of full-length OX40 (nucleotides 10–26).

The PCR conditions were: one cycle at 94° C. For 2 minutes, followed by 42° C. For two minutes; 30 cycles at 72° C. For 1.5 minutes, followed by 94° C. for one minute, then 48° C. for 1 minute; and one cycle at 72° C. for seven minutes. The resulting PCR product comprised the entire coding region of OX40, with Spe I restriction sites on each end.

The PCR product was digested with Spe I, and an approximately 800 by fragment was isolated by gel filtration, and used in a second round of PCR reaction. The isolated fragment was ligated into Spe I cut plasmid, pBLUESCRIPT SK® (Stratagene Cloning Systems, La Jolla, Calif.), which had been treated with calf intestine alkaline phosphatase (CIAP) to prevent self-ligation. This plasmid was used to PCR an extracellular region of murine OX40; the nucleotide and predicted amino acid sequence of the extracellular domain of mouse OX40 are presented in SEQ ID NOs: 6 and 7.

The oligonucleotide primers used in the PCR reaction were those represented in SEQ ID NO: 3 (5') and SEQ ID NO: 5 (3'). SEQ ID NO: 3 is described above; the oligonucleotide defined by SEQ ID NO: 5 deletes the region of murine OX40 that corresponds to the transmembrane region of rat OX40 as described by Mallett et al., and five addition, C-terminal amino acids that are part of the extracellular region. The oligonucleotide represented by SEQ ID NO: 5 also includes a Bgl II site, and a sequence encoding two amino acids from the N-terminal of an Fc region of a human IgG$_1$.

The PCR conditions were: five cycles at 94° C. for one minute, followed by 42° C. for one minute, then 72° C. for one minute; 25 cycles at 94° C. for one minute, followed by 50° C. for one minute, then 72° C. for one minute; and one cycle at 72° C. for seven minutes. An aliquot of the PCR reaction was reamplified in another round of PCR, with the following conditions: 20 cycles at 94° C. for one minute, followed by 55° C. for one minute, then 72° C. for one minute; and one cycle at 72° C. for seven minutes.

The resulting final PCR product was digested with Spe I/Bgl II, and isolated by gel filtration, to yield a fragment of approximately 630 bp. The PCT product was used in a three-way ligation with a Bgl II/Spe I fragment of a DNA encoding a human IgG Fc, into Spe I cut pBLUESCRIPT SK®. After amplification in *E. coli*, the insert encoding the OX40/Fc fusion protein was digested with Sal I/Not I, and cloned into plasmid pDC406 (McMahan et al., *EMBO J.* 10:2821, 1991) which had also been cut with Sal I/Not I. The pDC406 plasmid includes regulatory sequences derived from SV40, human immunodeficiency virus (HIV), and Epstein-Barr virus (EBV), and is also replicable in *E. coli*. The resulting plasmid was designated pDC406/OX40/Fc.

EXAMPLE 2

This example describes construction of an OX40/Fe mutein fusion protein construct to express a soluble OX40/Fc mutein fusion protein for use in detecting cDNA clones encoding an OX40 ligand. pDC406/OX40/Fc was used for site-directed mutagenesis, using a commercially-available kit, Clonetech (Palo Alto, Calif, USA) substantially as described by Ray and Nickoloff, *Biotechniques* 13:342 (1992) and Deng and Nickoloff, *Anal, Biochem.* 200:81 (1992). Three amino acid residues in the Fc region were changed (Leu234 to Ala, Leu235 to Glu and Gly237 to Ala, using the amino acid numbering of Canfield and Morrison, *J. Exp. Med.* 173:1483; 1991).

Briefly, two mutangenic oligonucleotide primers were prepared. The first primer (SEQ ID NO: 8) contained the desired mutations, changing the codon CTC (encoding Leu), to GCC (encoding Ala); changing the codon CTG (encoding Leu) to GAG (encoding Glu), and the codon GGA (encoding Gly) to GCG (encoding Ala). The second primer (SEQ ID NO: 9) contained a mutation in a unique restriction site, Pvu I. This restriction site is found in the ampicillin resistance gene of pDC406 at position 3542.

The resulting DNA was transformed into a mismatch repair defective *E. coli* strain BMH 71-18 mutS to increase the probability that the two mutations would not be removed by in vivo DNA repair mechanisms, and would cosegregate during the first round of DNA replication. Transformants were selected using ampicillin, and plasmid DNA prepared. The plasmid DNA was treated with the enzyme Pvu I, to linearize parential molecules and thereby reduce the efficiency of the parental molecules to transform bacteria. Plasmids the contained the mutation were not linearized, and were able to transform bacteria efficiently, allowing facile amplification of the plasmid encoding the OX40/Fc mutein. Following transformation of *E. coli* strain DH10B, amplified plasmid DNA was prepared. A clone was isolated which contained mutations at the appropriate residues in the Fc portion of the sequence, and which had lost the unique Pvu I site.

The plasmid encoding the resulting mutein was referred to as pDC406/OX40/Fc*. The nucleotide and predicted amino acid sequence of pDC406/OX40/Fc* are shown in SEQ ID NOs: 10 and 11, the protein encoded thereby is referred to as OX40/Fc mutein. The resulting OX40/Fc mutein exhibited reduced affinity for immunoglobulin receptors. The mutant amino acids designated 234, 235 and 237 by Canfield and Morrison, supra, correspond to amino acids 225, 226 and 228, respectively, of SEQ ID NOs: 10 and 11.

pDC406/OX40/Fc* was transfected into the monkey kidney cell line CV-1/EBNA (ATCC CRL 10478). The CV-1/EBNA cell line was derived by transfection of the CV-1 cell line with a gene encoding Epstein-Barr virus nuclear antigen-1 (EBNA-1) that constitutively expresses EBNA-1 driven from the human CMV intermediate-early enhancer/promoter. The EBNA-1 gene allows for episomal replication of expression vectors, such as pDC406, that contain the EBV origin of replications.

Once cells expressing the fusion construct were identified, large scale cultures of transfected cells were grown to accumulate supernatant from cells expressing OX40/Fc mutein. The OX40/Fc mutein in supernatant fluid was purified by affinity purification. Briefly, culture supernatant containing the OX40/Fc fusion protein was purified by filtering mammalian cell supernatants (e.g., in a 0.45μ filter) and applying filtrate to a protein A antibody affinity column (BioRad, Richmond, Calif., USA) at 4° C. at a flow rate of approximately 80 ml/hr for a 1.5 cm×12.0 cm column. The column was washed with PBS (phosphate buffered saline) until free protein could not be detected in wash buffer. Bound OX40/Fc mutein was eluted from the column with 50 mM citrate buffer, pH 2.8, and brought to pH 7 with 5N NaOH. Silver-stained SDS gels of the eluted OX40Fc mutein showed it to be >90% pure.

EXAMPLE 3

This example describes selection of a cell line putatively expressing membrane-bound OX40-L. Several cell lines were screened using OX40/Fc mutein prepared according to Example 2, and biotin-labeled goat anti-human IgG antibody (Jackson Labs, Bar Harbor, Me.). Briefly, several different cell lines were analyzed according to standard methodology for flow cytometry. A clonal cell lines, S49.1 (ATCC TIB 128; a murine T cell lymphoma line) was found to express approximately 1000 molecules of putative OX40-L per cell. The cell line as subjected to several rounds of sorting using flow cytometry, in order to enrich for a population that expressed high levels of the putative OX40-L. Cells from the fourth round of sorting, referred to as OX49.4, were cultured and found to express approximately 15,000 molecules of OX40-L per cell.

EXAMPLE 4

This example describes preparation of a cDNA library for expression cloning of muOX40-L. The cDNA expression library was made essentially as described in U.S. Pat. No. 4,968,607, the disclosure of which is incorporated by reference herein. Briefly, murine lymphoma cells from the line S49.1 (ATCC TIB 128) were incubated for 6 hours in 10 ng/ml of the phorbol ester myristic acid (PMA), and RNA was isolated by isothiocyanate extraction and ultracentifugation as described in Chirgwin et al. *Biochem.* 18:5294 (1979) and Sambrook et al., *Molecular Cloning: A Laboratory Manual,* Cold Spring Harbor Press, Cold Spring Harbor, New York, second ed. (1989).

Poly A⁺ mRNA was isolated by oligo dT cellulose chromatography (Aviv and Leder, *Proc. Natl. Acad. Sci. USA* 69:1408, 1972) and double stranded cDNA made substantially as described by Gubler et al. *Gene* 25:263, 1983. Poly A⁺ mRNAs were converted to RNA-cDNA hybrids with the enzyme reverse transcriptase using random hexanucloetide primers. The RNA-cDNA hybrids were then converted to double-stranded cDNA fragments using RNaseH in combination with *E. coli* DNA polymerase I. The double-stranded cDNA ends were rendered blunt with Klenow fragment of polymerase I.

The following primers #1 and #2, capable of ligating to a digested Bgl II site, were used to adaptor the cDNA and cloning vector essentially as described in Haymerle et al. *Nucl. Acids Res.* 14:8615, (1986):
1 5'-GATCTTGGAACGAGACGACCTGCT-3'OH SEQ ID NO: 12
2 5'-AGCAGGTCGTCTCGTTCCAA-3'OH SEQ ID NO: 13

After annealing the primers were ligated to the 5' ends of the blunt-ended cDNAs, and the non-ligated adaptors and complementary strands (primer #2) were removed by gel filtration chromatography at 68° C. This left single strand 24 nucleotide overhangs on the cDNA which were non-self complementary. The same procedure was used to ligate primer #2 to the 5'Bgl II ends of the mammalian expression vector pDC410 (a derivative of pDC406 (McMahan et al., *EMBO J.* 10:2821, 1991) with a unique Bgl II site and bearing the SV40 T antigen gene) to create 24 nucleotide overhangs complementary to those added to the cDNA. Optimal proportions of vector and cDNA were then ligated with T4 DNA ligase in the presence of T4 polynucleotide kinase. Dialyzed ligations mixtures were introduced into *E. coli* strain DH5α (Bethesda Research Laboratories, *Bethesda Res. Focus* 8(2): 9, 1986) by electroporation. Transformants were selected on ampicillin plates.

Plasmid DNA was isolated from pools consisting of approximately 2,000 *E. coli* clones per pool. The isolated DNA was transfected into a sub-confluent layer of CV-1/EBNa cells (McMahan et al. *EMBO J.* 10:2821, 1991) using DEAE-dextran in chloroquine containing media followed by DMSO shock, substantially according to the procedures described in Luthman et al., *Nucl. Acids Res.* 11:295 (1983) and McCutchan et al., *J. Natl. Cancer Inst.* 41:351 (1986).

CV-1/EBNA cells were maintained in complete medium (Dulbecco's modified Eagles' media containing 10% v/v fetal calf serum, 50 U/ml streptomycin, and 2 mM L-glutamine) and were plated to a density of approximately $2 \times 10^5$ cells/well in a single-well chambered slides that had been pre-treated with 1 ml human fibronectin solution (10 µg/ml in PBS) for 30 minutes. After approximately 24 hours growth media was removed from the adherent layer of cells and replaced with 1.5 ml complete media containing 66.6 µM chloroquine sulfate. DNA solution (0.2 ml with 2.0 µg DNA and 0.5 mg/ml DEAE-dextran in complete media plus chloroquine) was added to the cells. The mixture was incubated at 37° C. for 4.5 hours prior to shocking the cells by the addition of complete media containing 10% dimethylsulphoxide for approximately 5 minutes.

EXAMPLE 5

This example describes the screening of the expression library made in Example 4 by slide autoradiography (Gearing et al., *EMBO J* 8:3667, 1989) to detect OX40-L expression. OX40/Fc mutein fusion protein made in Example 2 was used in combination with $^{125}$I-labeled anti-human IgG F(ab)₂ antibody to detect fusion protein bound to the ligand.

Murine anti-human IgG Fc (F(ab)₂ (Jackson Labs, Bar Harbor, Me.) was radio-iodinated to a specific activity of $5-15 \times 10^{15}$ cpm/mmol using chloramine-T catalysis and removal of unincorporated $^{125}$-I by gel filtration as follows. A chloramine-T solution of 2 mg/ml was freshly prepared in 0.05M sodium phosphate buffer (pH 7.2) and 15 µl added to each of 2 microfuge tubes containing 5 µg of the anti-human IgG Fc (F(ab)₂ fragment in approximately 5 µl PBS, followed by 2 millicuries of Na $^{125}$I (added in 20 µl of 0.05M sodium phosphate buffer (pH 7.2). The mixture was incubated for 30 minutes at room temperature and then applied to a Sephadex G-25 column that had been packed according to manufacturer's instructions, and washed with 5 volumes of PBS. The radiolabeled anti-human IgG Fc (F(ab)₂ was eluted from the column in approximately 100 µl fractions, the peak fractions pooled, and diluted to 4 ml in binding medium that lacked non-fat dry milk (RPMI 1640 containing 25 mg/ml bovine serum albumin (BSA), 2 mg/ml sodium axide, 20 mM HEPES pH 7.2). Level of incorporation was determined by quantitating the cpm in a measured aliquot and in a trichloroacetic acid (TCA) precipitate of the aliquot with a gamma counter. The labeled protein was ≧95% TCA precipitable, indicating that the $^{125}$I was covalently bound to the protein.

CV-1/EBNA cell monolayers were transfected with DNA from cDNA library pools on slides as in Example 3 and incubated 48–72 hours to allow OX40-L expression. The cell layers were washed once with binding medium (RPMI 1640 containing 25 mg/ml bovine serum albumin (BSA), 2 mg/ml sodium axide, 20 mM HEPES pH 7.2, and 50 mg/ml nonfat dry milk) that contained reagents to block binding to cellular Fc receptors (20% v/v complement-inactivated calf serum and 25 mg/ml monoclonal anti-murine Fc receptor antibody 2.4G2 (ATCC HB197)). The cells were then incubated in this medium containing 1 µg/ml OX40/Fc mutein fusion protein for 1 hours at room temperature.

After removal of the OX40/Fc-containing medium, the cells were washed 2 times in binding medium, then incubated for 30 minutes at room temperature in binding medium containing approximately $2 \times 10^{-9}$M $^{125}$I-murine anti-human Fc (F(ab)₂ fragment labeled as described above. The cells were then washed 3 times with binding medium, 2 times with PBS, and fixed by incubation for 30 minutes at room temperature in 1 ml 2.5% glutaraldehyde in PBS.

Autoradiography as then performed by dipping the slides in Kodak GTNB-2 photographic emulsion (6 X dilution in water) and exposure in the dark for 3–4 days at room temperature. The slides were developed for 4 minutes in Kodak GBX developer (40 g/500 ml water), rinsed for 30 seconds in water, and fixed in Kodak rapid fixer for 4 minutes. Slides were viewed at 25–40 X magnification by microscope and cells expressing OX40L were detected by the presence of dark autoradiographic silver grains.

Using slide audioradiography, approximately 500,000 cDNAs were screened as pools of approximately 2000 to yield 4 pools positive for OX40/Fc mutein binding. An OX40L cDNA was then isolated from one pool, #198, as follows. *E. coli* cells from #198 were plated on growth medium with ampicillin to generate 25 smaller sub-pools of approximately 250, and DNA was isolated from the sub-pools.

Each sub-pool was transfected into CV-1/EBNA monolayers, and the monolayers subjected to slide autoradiography as above, with the exception that prior to dipping in photographic emulsion the slides were also exposed on a Phosphoimager (Molecular Dynamics) overnight to aid detection of sub-pools that expressed OX40-L. Cells from individual clones of one positive subpool were picked into liquid medium in a row and column format in a microtiter plate, followed by incubation at 37° C. to allow growth.

100 μl aliquots were removed from the cultures and pooled for members of a row or column. DNAs were prepared from the row and column pools, and transfected into CV-1/EBNA cells on slides substantially as described previously; slide autoradiography was performed on the transfected cells as described above. One row and one column were positive, and defined a single clone, #198-13-33(™33), containing an OX40-L cDNA. The cDNA insert in clone #33 was 1476 bp as determined by dideoxynucleotide sequencing.

A second OX40-L cDNA clone (#69-9-2) was isolated from positive pool #69 by generating positive sub-pools as described above and screening colonies from the sub-pools by colony hybridization (Grunstein and Hogness, *Proc. Natl. Acad. Sci.* USA 72:3961, 1975) with a radioactive OX40-L probe, generated from clone #33 by polymerase chain reaction (Saiki et al *Science* 239:487, 1988) in the presence of $^{32}\alpha$-P-dCTP. The cDNA insert in clone #69-9-2 was extended by 110 bp in the 5' region of the OX40-L cDNA as compared to clone #33, for a total length of was 1586 bp as determined by dideoxynucleotide sequencing. The complete nucleotide and the amino acid coding region for OX40-L derived from it are depicted in SEQ ID NOs: 1 and 2, respectively. The coding region for clone #69-9-2 is predicted to begin with nucleotide 148, extending to a stop codon (nucleotides 742–744). Clone #69-9-2 exhibits an open reading frame of 122 bases 5' to the putative initiator methionine (nucleotides 26–147 of SEQ ID NO: 1).

EXAMPLE 6

This example describes the screening for OX40-L cDNA clones with extended 5' ends compared to clone #69-9-2 by first generating OX40-L single stranded cDNAs, and then using a 5' anchored PCR technique substantially as described by Loh et al. *Science* 243:217, 1989.

Briefly, starting with RNA containing OX40-L transcript, such as poly $A^+$ RNA isolated from S49.1 cells, reverse transcriptase is used to generate cDNA/RNA hybrids with a primer specific for OX40-L mRNA and complementary to the 3' non-coding region of the OX40-L coding strand. After removal of RNA, the DNA strand is extended by incubating with terminal deoxyribonucleotidyl transferase in the presence of a single deoxynucleotide triphosphate such as dATP. PCR is then initiated to amplify these cDNAs using primers specific for the cDNA strand. In one embodiment, a primer consisting of poly dT and, for purposes of cloning, a 17-mer oligonucleotide including a Not I site at its 5' end is used to prime a strand complementary to the cDNA. This double-stranded DNA product is then amplified by PCR using both the dT containing primer and an excess of a shorter oligonucleotide primer consisting of the non-poly dT bases in combination with a third primer containing a Not I site and bases complementary to the stop codon and the 3' end of the OX40-L coding region.

The amplified product is digested with Not I restriction enzyme and cloned into a Not I digested *E. coli* cloning vector, such as pBluescript SK®. Clones containing an OX40-L cDNA insert are detected by filter hybridization with a oligonucleotide complementary to the 5' end of the OX40-L coding region that was labeled with $^{32}P$ by the enzyme T4 polynucleotide kinase (Sambrook et al. *Molecular Cloning: A Laboratory Manual*, Cold Spring Harbor Press, Cold Spring Harbor, N.Y. second ed. (1989)).

A number of techniques may then be used to detect cDNAs with 5' extensions as compared to clone #69-9-2. In one embodiment, an oligonucleotide primer complementary to the 5' end of the coding region is used, together with an oligonucleotide primer complementary to vector sequences adjacent the cDNA insert, to again perform anchored PCR so that the 5' region of cDNA clones is amplified. The products of the PCR reactions are examined by gel electrophoresis and their length compared with a similarly derived amplification product from clone #69-9-2. The cDNA inserts for those clones giving longer 5' PCR product are then sequenced in their entirety by standard dideoxynucleotide sequencing techniques to determine if a longer OX40-L polypeptide is encoded by the cDNAs.

EXAMPLE 7

This example describes the bioaffinity immunoprecipitation of OX40-L from cells expressing OX40-L. OX49.4 cells, or PMA-stimulated S49.1 cells, were surface labeled with Biotin X-NHS. Briefly, cells were washed with phosphate-buffered saline (PBS), and treated with 100 μg biotin-X-NHS (CalBiochem, San Diego, Calif. USA) per $10^7$ cells, at pH 7.4 for 30 minutes. The treated cells were then washed with PBS to remove the excess unconjugated biotin, and lysed with 1% Triton X-100/300 Kallikrein units per ml aprotinin-A/5 mM EGTA.

Lysates were incubated with 10 μg/ml OX40Fc mutein prepared as described in Example 2 (or a control, CD40/Fc protein) for at least two hours at 4° C., with intermittent agitation, to allow the receptor and ligand to form a matrix. In some experiments, the incubation length was up to about 16 hours. Protein-A/G agarose (Pierce, Rockford, Ill.; USA) was added, and the lysate mixture was incubated one hour at 4° C. to form a precipitable protein A/G-Fc-receptor-ligand matrix.

The precipitable matrix was pelleted by centrifugation, washed extensively in 10 mM HEPES, 0.5% NP-40, and PBS, and resuspended in Laemmili reducing sample buffer. Samples of the precipitable matrix were solubilized by boiling, added to 4–20% gradient acrylamide gels, and electrophoresed under reducing conditions. Bioaffinity immunoprecipitation of labeled OX49.4 or PMA-stimulated S49.1 cells with OX40/Fc mutein resulted in the identification of an abundant, distinct, putative OX40-L protein of approximately 30 Kd in the OX49.4 cells, and a lesser amount of the same Mr protein from the stimulated S49.1 cells, that correlated with surface expression of OX40-L. This protein was not observed in samples that had been incubated with the control CD40/Fc protein.

EXAMPLE 8

This example illustrates T cell proliferative activity of membrane-bound murine OX40-L for murine (mouse and rat) cells. Lymphoid organs were harvested aseptically and cell suspensions were prepared as described (Fanslow et al., *J. Immunol.* 147:535; 1991). Mouse T cells were isolated from spleens of C57B1/6 mice and purified by incubating with monoclonal antibodies against CD11b (Mac-1; Springer et al., *Eur. J. Immunol.* 9:301; 1979) and class II MHC (25-9-17; Ozato et al., *J. Immunol.* 126:317; 1981) for 30 minutes 4° C., loading the incubated cell preparations onto a T cell purification column (Pierce, Rockford, Ill., USA), and eluting the T cells according to the manufacturer's instructions. Rat T cells were purified from the spleens of Lewis rats by negative selection using sheep anti-rat IgG coated magnetic beads (Dynal, Bioproducts for Science, Indianapolis, Ind., USA) to remove the rat B cells and monocytes.

T cell proliferation assays were set up in round- or -flat bottomed 96-well plates using 0.5 to $1.5 \times 10^5$ cells per well. Mouse T cells were cultured in the presence of a sub-optimal level (0.5 μg/ml) of concanvalin A (Con A; Sigma, St. Louis, Mo., USA); rat T cells were cultured in the presence of sub-optimal levels of phytohemmagglutinin (PHA; Difco, Detroit, Mich. USA), either 0.5% w/v or 1.0% w/v PHA. Both rat and mouse T cell cultures also included CV-1/EBNA cells transfected either with murine OX40-L cDNA or vector alone (HAVEO), prepared as described in Example 5, and fixed at two days post-transfection with 1% paraformaldehyde for five minutes at 25° C. The T cells were pulsed with 1 μCi/well of tritiated thymidine (25 Ci/nmole, Amersham, Arlington Heights, Ill., USA) for the final eighteen hours of a three day culture. T cells were harvested onto glass fiber discs with an automated cell harvester and incorporated radioactivity was measured using a Matrix 96 beta counter (Packard-Bell, Meridian, Conn., USA).

Figure 2:
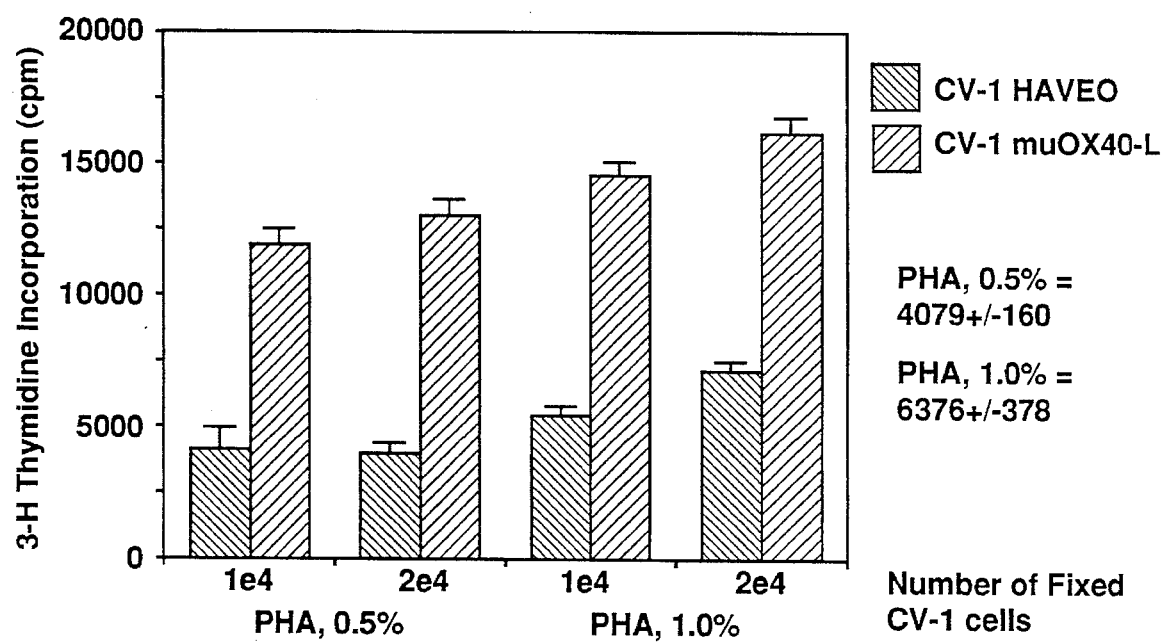
FIG. 2 illustrates the effect of fixed CV-1/EBNA cells transfected with an expression vector encoding mouse OX40-L versus fixed CV-1/EBNA cells transfected with vector alone on the proliferation of rat T cells in the presence of suboptimal levels of mitogen (Phytohemmagglutinin at either 0.5% w/v or 1.0% w/v).

FIG. 1 shows a comparison of mouse T cell proliferation by CV1 EBNA cells transfected with vector alone (HAVEO) or with murine OX40-L cDNA in HAVEO vector. These data show that membrane-bound OX40-L stimulates mouse T cell proliferation in the presence of a suboptimal level of a co-mitogen. FIG. 2 shows a comparison of rat T cell proliferation by CV1 EBNA cells transfected with vector alone (HAVEO) or with murine OX40-L cDNA in HAVEO vector. These data show that membrane-bound OX40-L stimulates rat T cell proliferation in the presence of suboptimal levels of a co-mitogen. Accordingly, membrane-bound OX40-L co-stimulates proliferation of murine T cells.

EXAMPLE 9

This example illustrates the ability of membrane-bound murine OX40-L to stimulate cytokine secretion from murine T cells. Purified lymph node T cells from C57B1/6 mice (a mixture of both CD4+ and CD8+ cells; approximately $1 \times 10^5$ cells/well) were incubated in microtiter wells left untreated (medium) or coated with 0.2 μg/ml anti-TCRαβ H57-597; Kubo et al., *J. Immunol.* 142:2736; 1989). In addition to the lymphocytes, wells contained either no addition (TCR) or CV-1/EBNA cells ($10^4$/well) transfected with murine OX40-L cDNA or vector alone (HAVEO), as described previously, or the wells also contained IL-2 (5 ng/ml: Immunex, Seattle, Wash., USA) or anti-CD28 ascites (37.5; Gross et al., *J. Immunol.* 149:380; 1992) diluted 1:1000. Culture supernatant was harvested from these cultures after 48 hours, and analyzed for the presence of IL-2 and/or IL-4, IL-2 and IL-4 levels were measured by bioassay usng using the IL-2 and IL-4 dependent cell lines CTLL-2 (Gillis et al., *J. Immunol.* 120:2027; 1978) and CT.4S (Hu-Li et al., *J. Immunol.* 142:800; 1989). Proliferation of the CTLL-2 and CT.4S cells was measured after 36 hours of culture with the supernatant harvested from the T cell cultures, using a standard $^3$H-thymidine incorporation assay.

Figure 3:
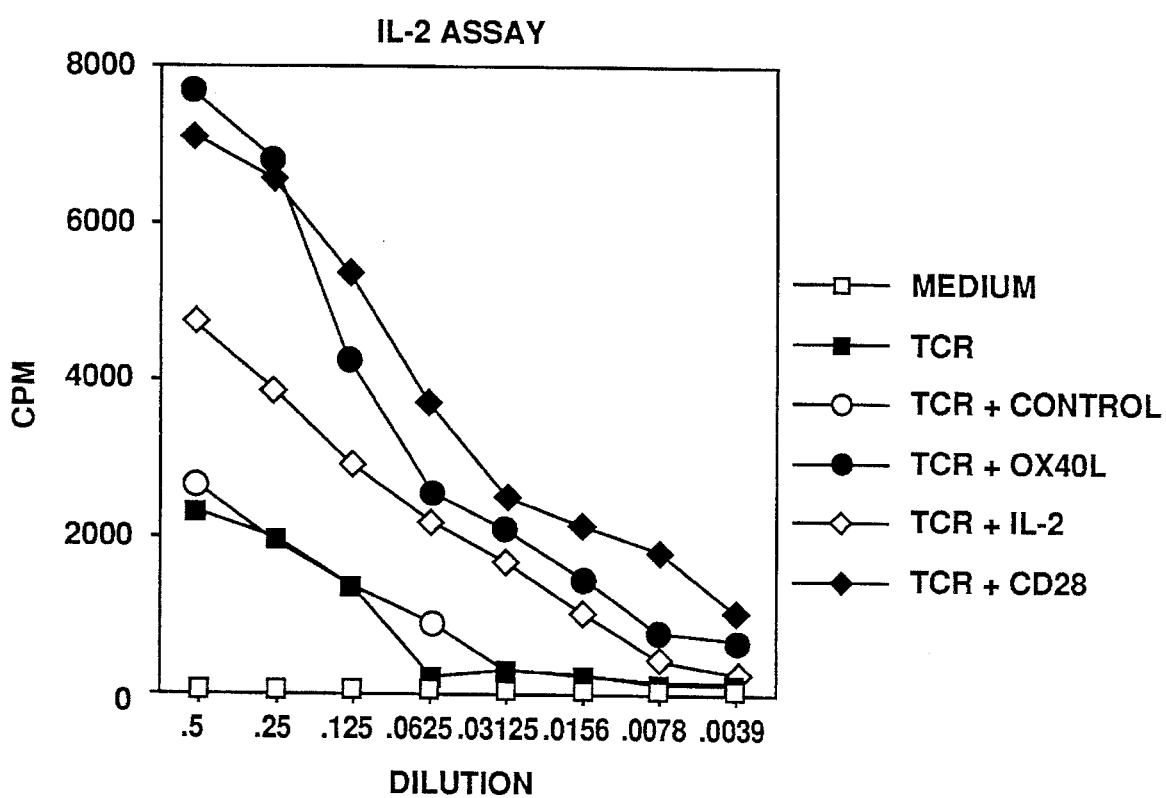
FIG. 3 illustrates the effect of fixed CV-1/EBNA cells transfected with an expression vector encoding mouse OX40-L versus fixed CV-1/EBNA cells transfected with vector alone on the secretion of IL-2 by mouse T cells.
Figure 4:
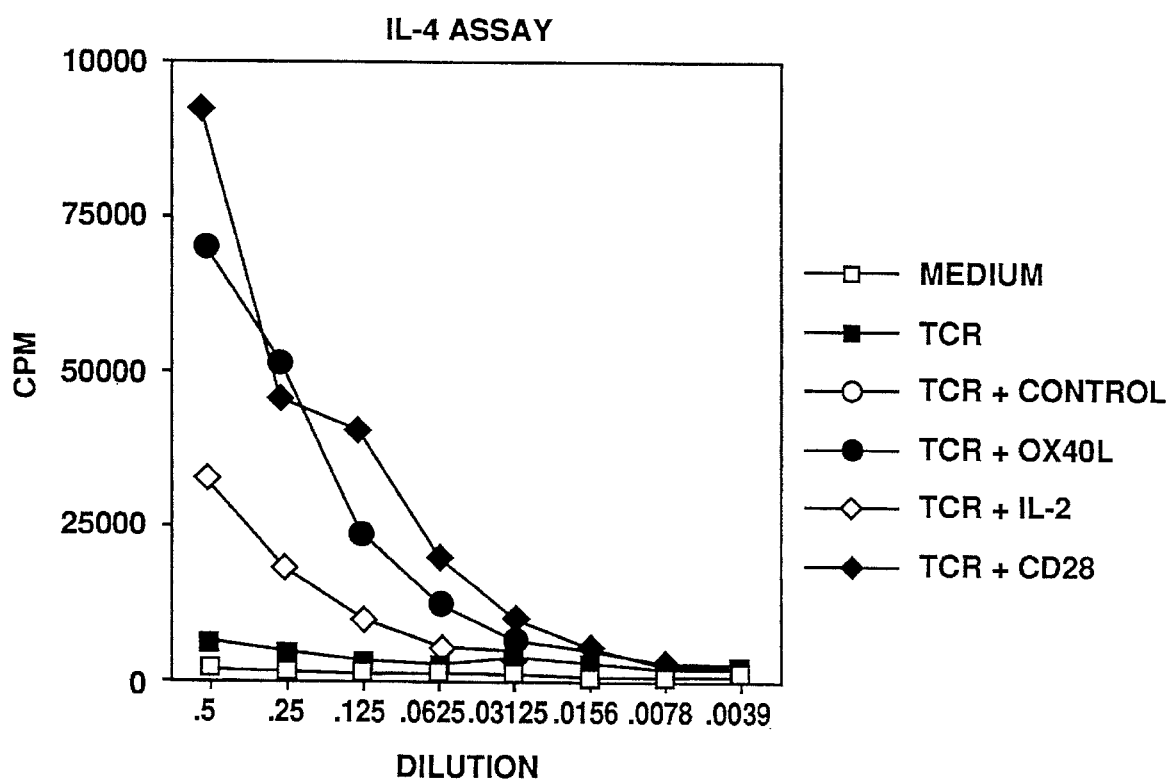
FIG. 4 illustrates the effect of fixed CV-1/EBNA cells transfected with an expression vector encoding mouse OX40-L versus fixed CV-1/EBNA cells transfected with vector alone on the secretion of IL-4 by mouse T cells.

FIG. 3 illustrates the proliferation of CTLL-2 cells, an IL-2-dependent cell lines, in response to the harvested supernatants. FIG. 4 shows the proliferation of CT.4S cells, an IL-4-dependent cell lines, in response to the harvested supernatants. Taken together, the results demonstrate that OX40-L is a potent co-stimulus for IL-2 and IL-4 production in T cells. Further, the ability of OX40-L to induce levels of IL-2 and IL-4 similar to those induced in the presence of anti-CD28 suggests that OX40-L provides an extremely potent co-stimulatory signal.

EXAMPLE 10

This example illustrates the preparation of monoclonal antibodies to OX40-L. OX40-L is expressed in mammalian cells such as COS-7 or CV-1/EBNA cells, and purified using OX40/Fc affinity purification. Purified OX40-L, fragments thereof (such as the extracellular domain), synthetic peptides, or cells over-expressing OX40-L can be used as immunogens to generate monoclonal antibodies against OX40-L using conventional techniques, for example, those techniques described in U.S. Pat. No. 4,411,993. Briefly, mice are immunized with OX40-L as an immunogen emulsified in complete Freund's adjuvant, and injected in amounts ranging from 10–100 μg subcataneously or intraperitoneally. Ten to twelve days later, the immunized animals are boosted with additional OX40-L emulsified in incomplete Freund's adjuvant. Mice are periodically boosted thereafter on a weekly to bi-weekly immunization schedule. Serum samples are periodically taken by retroorbital bleeding or tail-tip excision for testing by dot blot assay, ELISA (enzyme-Linked Immunosorbent Assay), or inhibition of OX40-L binding, for OX40-L antibodies.

Following detection of an appropriate antibody titer, positive animals are provided one last intravenous injection of OX40-L in saline. Three to four days later, the animals are sacrificed, spleen cells harvested, and spleen cells are fused to a murine myeloma cell line (e.g., NS1 or preferably Ag 8.653 [ATCC CRL 1580]). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified OX40-L by adaptations of the techniques disclosed in Engvall et al., *Immunochem.* 8:871, 1971 and in U.S. Pat. No. 4,703,004. A preferred screening technique is the antibody capture technique described by Beckman et al., *J. Immunol.* 144:4212 (1990). Positive hybridoma cells can be injected intraperitoneally into syngeneic BABL/c mice to produce ascites containing high concentrations of anti-OX40-L monoclonal antibodies. Alternatively, hybridoma cells can be grown in vitro in flasks or roller bottles by various techniques. Monoclonal antibodies produced in mouse ascites can be purified ammonium sulfate precipitation, followed by gel exclusion chromatography. Alternatively, affinity chromatography based upon binding of antibody to protein A or protein G can also be used, as can affinity chromatography based upon binding to OX40-L.

What is claimed is:

1. An isolated DNA encoding an OX40 ligand polypeptide that binds to OX40, wherein the DNA is selected from the group consisting of:
   (a) nucleotides 148 through 741 of SEQ ID NO: 1; and
   (b) DNA sequences which, due to degeneracy of the genetic code, encode a polypeptide encoded by the foregoing DNA sequence, wherein the OX40 ligand polypeptide binds OX40.

2. An isolated DNA sequence according to claim 1 encoding a soluble OX40 ligand polypeptide.

3. A recombinant expression vector comprising a DNA sequence according to claim 1.

4. A recombinant expression vector comprising a DNA sequence according to claim 2.

5. A host cell transformed or transfected with an expression vector according to claim 3.

6. A host cell transformed or transfected with an expression vector according to claim 4.

7. A process for preparing a OX40-L polypeptide, comprising culturing a host cell according to claim 5 under conditions promoting expression and recovering OX40 ligand polypeptide from the culture.

8. A process for preparing a OX40-L polypeptide, comprising culturing a host cell according to claim 6 under conditions promoting expression and recovering OX40 ligand polypeptide from the culture.

* * * * *